US011065350B2

(12) United States Patent
Dunphy et al.

(10) Patent No.: US 11,065,350 B2
(45) Date of Patent: Jul. 20, 2021

(54) HSP90-TARGETED INFLAMMATION AND INFECTION IMAGING AND THERAPY

(71) Applicant: Memorial Sloan Kettering Cancer Center, New York, NY (US)

(72) Inventors: Mark Dunphy, New York, NY (US); Gabriela Chiosis, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 16/845,372

(22) Filed: Apr. 10, 2020

(65) Prior Publication Data

US 2020/0237934 A1   Jul. 30, 2020

Related U.S. Application Data

(63) Continuation of application No. 15/511,701, filed as application No. PCT/US2015/050753 on Sep. 17, 2015, now Pat. No. 10,617,772.

(60) Provisional application No. 62/051,590, filed on Sep. 17, 2014.

(51) Int. Cl.
| | |
|---|---|
| *A61K 51/04* | (2006.01) |
| *A61P 35/00* | (2006.01) |
| *A61K 49/00* | (2006.01) |
| *A61B 5/00* | (2006.01) |
| *A61K 31/52* | (2006.01) |
| *A61B 5/318* | (2021.01) |
| *A61B 5/0275* | (2006.01) |
| *A61B 5/08* | (2006.01) |
| *A61B 6/03* | (2006.01) |
| *A61B 6/00* | (2006.01) |
| *A61K 49/18* | (2006.01) |

(52) U.S. Cl.
CPC ...... *A61K 51/0459* (2013.01); *A61B 5/02755* (2013.01); *A61B 5/0813* (2013.01); *A61B 5/318* (2021.01); *A61B 5/4255* (2013.01); *A61B 5/441* (2013.01); *A61B 6/032* (2013.01); *A61B 6/037* (2013.01); *A61B 6/4417* (2013.01); *A61B 6/503* (2013.01); *A61B 6/5288* (2013.01); *A61B 6/541* (2013.01); *A61K 31/52* (2013.01); *A61K 49/0004* (2013.01); *A61K 49/1884* (2013.01); *A61P 35/00* (2018.01)

(58) Field of Classification Search
CPC .... A61K 51/00; A61K 51/0459; A61K 49/00; A61K 49/1884; A61K 31/00; A61K 31/52; A61K 49/0004; A61B 6/503; A61B 5/02755; A61B 5/441; A61B 6/032; A61B 5/4255; A61B 6/4417; A61B 6/037; A61B 6/541; A61B 6/5288; A61B 5/318; A61P 35/00

USPC .... 424/1.11, 1.65, 1.81, 1.85, 1.89, 9.1, 9.2; 514/1, 1.1, 19.2, 19.3, 19.4, 19.5, 19.6
See application file for complete search history.

(56) References Cited

U.S. PATENT DOCUMENTS

| | | | |
|---|---|---|---|
| 7,834,181 B2 | 11/2010 | Chiosis et al. | |
| 8,178,687 B2 | 5/2012 | Alasia et al. | |
| 8,324,240 B2 | 12/2012 | Cai et al. | |
| 8,669,248 B1 | 3/2014 | Montana et al. | |
| 8,703,942 B2 | 4/2014 | Chiosis et al. | |
| 9,328,114 B2* | 5/2016 | Chiosis | ................ A61K 31/52 |
| 9,346,808 B2 | 5/2016 | Sun et al. | |
| 9,403,828 B2 | 8/2016 | Chiosis | |
| 9,546,170 B2 | 1/2017 | Taldone et al. | |
| 9,555,137 B2* | 1/2017 | Chiosis | ............ G01N 33/57426 |
| 9,567,318 B2 | 2/2017 | Chiosis et al. | |
| 9,701,678 B2 | 7/2017 | Chiosis et al. | |
| 9,926,321 B2 | 3/2018 | Sun et al. | |
| 9,956,293 B2* | 5/2018 | Chimmanamada | .. A61K 31/704 |
| 10,000,494 B2 | 6/2018 | Chiosis | |
| 10,064,867 B2 | 9/2018 | Taldone et al. | |
| 10,172,863 B2* | 1/2019 | Chiosis | ................ A61P 35/02 |
| 10,201,623 B2* | 2/2019 | Dunphy | ................ G01N 33/60 |
| 10,329,293 B2* | 6/2019 | Ochiana | ................ C07F 7/2208 |

(Continued)

FOREIGN PATENT DOCUMENTS

| | | |
|---|---|---|
| WO | WO-2004/097428 A1 | 11/2004 |
| WO | WO-2006/084030 A2 | 8/2006 |

(Continued)

OTHER PUBLICATIONS

Nichols et al, Clinical Microbiology Reviews, vol. 21, No. 2, pp. 274-290 (Year: 2008).*

(Continued)

*Primary Examiner* — D. L. Jones
(74) *Attorney, Agent, or Firm* — Choate, Hall & Stewart LLP; Brenda Herschbach Jarrell; John P. Rearick

(57) ABSTRACT

The present invention provides new methods for inflammation and infection imaging and related medical applications thereof. In some embodiments, the present invention provides a method for the diagnosis of inflammation and/or infection. In some embodiments, the present invention provides a method for the treatment or prevention of inflammation and/or infection. In some embodiments, the present invention provides methods for monitoring the effect of inflammation and/or infection treatment, and/or methods for monitoring an inflammation and/or infection treatment regimen. In some embodiments, the present invention provides a method for selecting subjects for an inflammation and/or infection treatment. In some embodiments, the present invention provides a method for determining the dosage of a drug for the treatment of inflammation and/or infection.

20 Claims, 4 Drawing Sheets

(56) References Cited

U.S. PATENT DOCUMENTS

| | | | |
|---|---|---|---|
| 10,336,757 B2* | 7/2019 | Chiosis | A61P 25/28 |
| 10,617,772 B2* | 4/2020 | Dunphy | A61B 6/4417 |
| 2005/0002861 A1 | 1/2005 | Krause et al. | |
| 2005/0107343 A1 | 5/2005 | Kasibhatla et al. | |
| 2008/0234314 A1 | 9/2008 | Cai et al. | |
| 2011/0104054 A1 | 5/2011 | Chiosis et al. | |
| 2011/0201587 A1 | 8/2011 | Shapiro | |
| 2011/0312980 A1 | 12/2011 | Chiosis | |
| 2012/0046266 A1 | 2/2012 | Brasca et al. | |
| 2012/0237508 A1 | 9/2012 | Cai et al. | |
| 2012/0252818 A1 | 10/2012 | Chiosis et al. | |
| 2012/0264770 A1 | 10/2012 | Co et al. | |
| 2012/0277257 A1 | 11/2012 | Yu et al. | |
| 2013/0045983 A1 | 2/2013 | Echeverria et al. | |
| 2013/0109684 A1 | 5/2013 | Blagg et al. | |
| 2014/0242602 A1 | 8/2014 | Chiosis et al. | |
| 2014/0294725 A1 | 10/2014 | Chiosis et al. | |
| 2014/0315929 A1 | 10/2014 | Chiosis | |
| 2016/0264577 A1 | 9/2016 | Sun et al. | |
| 2016/0310497 A1 | 10/2016 | Chiosis et al. | |
| 2016/0333014 A1 | 11/2016 | Chiosis | |
| 2017/0165265 A1 | 6/2017 | Chiosis et al. | |

FOREIGN PATENT DOCUMENTS

| | | |
|---|---|---|
| WO | WO-2006/098761 A2 | 9/2006 |
| WO | WO-2006/117669 A1 | 11/2006 |
| WO | WO-2006/123165 A2 | 11/2006 |
| WO | WO-2007/104944 A1 | 9/2007 |
| WO | WO-2007/134298 A2 | 11/2007 |
| WO | WO-2007/134677 A1 | 11/2007 |
| WO | WO-2008/005937 A2 | 1/2008 |
| WO | WO-2008/093075 A2 | 8/2008 |
| WO | WO-2008/115719 A1 | 9/2008 |
| WO | WO-2008/118391 A2 | 10/2008 |
| WO | WO-2009/097578 A1 | 8/2009 |
| WO | WO-2011/022440 A2 | 2/2011 |
| WO | WO-2011/044394 A1 | 4/2011 |
| WO | WO-2012/138894 A1 | 10/2012 |
| WO | WO-2012/138896 A1 | 10/2012 |
| WO | WO-2012/149493 A2 | 11/2012 |
| WO | WO-2013/009655 A2 | 1/2013 |
| WO | WO-2013/009657 A1 | 1/2013 |
| WO | WO-2014/025395 A1 | 2/2014 |
| WO | WO-2014/144715 A1 | 9/2014 |
| WO | WO-2015/023976 A2 | 2/2015 |

OTHER PUBLICATIONS

Louie et al, Emerging Infectious Diseases, vol. 10, No. 6, pp. 1143-1146 (Year: 2004).*
Barabustis, N. et al., LPS induces pp60c-src-mediated tyrosine phosphorylation of Hsp90 in lung vascular endothelial cells and mouse lung, Am J Physiol Lung Cell Mol Physiol, 304(12):L883-93 (2013).
Bohonowych, J. et al., Extracellular Hsp90 mediates an NF-κb dependent inflammatory stromal program: implications for the prostate tumor microenvironment, Prostate, 74(4):395-407 (2014).
Chen, D. et al., Luteolin exhibits anti-inflammatory effects by blocking the activity of heat shock protein 90 in macrophages, Biochem Biophys Res Commun, 443(1):326-32 (2014).
Collins, C. et al., Inhibition of N-terminal ATPase on HSP90 attenuates colitis through enhanced Treg function, Mucosal Immunol, 6(5):960-71 (2013).
Collins, C. et al., Targeted inhibition of heat shock protein 90 suppresses tumor necrosis factor-α and ameliorates murine intestinal inflammation, Inflamm Bowel Dis, 20(4):685-94 (2014).
International Search Report for PCT/US2015/50753, 3 pages (dated Dec. 18, 2015).
Jhaveri, K. and Modi, S., HSP90 inhibitors for cancer therapy and overcoming drug resistance, Adv. Pharmacol., 65:471-517 (2012).
Kakeda, M. et al., Increased expression of heat shock protein 90 in keratinocytes and mast cells in patients with psoriasis, J Am Acad Dermatol, 70(4):683-690 (2014).
Kim, N. et al., Anti-inflammatory properties and pharmacological induction of Hsp70 after brain injury, Inflammopharmacology, 20(3):177-185 (2012).
Petruzzi, N. et al., Recent trends in soft-tissue infection imaging, Semin Nucl Med, 39(2):115-23 (2009).
Rice, J. et al., Small Molecule Inhibitors of Hsp90 Potently Affect Inflammatory Disease Pathways and Exhibit Activity in Models of Rheumatoid Arthritis, Arthritis & Rheumatism, 58(12):3765-3775 (2008).
Shebrain, S. and Ramjit, A., Radicicol, a Hsp90 inhibitor, inhibits intestinal inflammation and leakage in abdominal sepsis, J Surg Res, 185(1):e53-4 (2013).
Taldone, T. et al., Design, synthesis, and evaluation of small molecule Hsp90 probes, Bioorg. Med. Chem., 19(8):2603-14 (2011).
Taldone, T. et al., Protein chaperones: a composition of matter review (2008-2013), Expert Opin Ther Pat, 24(5):501-18 (2014).
Thangjam, G. et al., Novel mechanism of attenuation of LPS-induced Nf-κb activation by the heat shock protein 90 inhibitor, 17-N-allylamino-17-demethoxygeldanamycin, in human lung microvascular endothelial cells, Am J Respir Cell Mol Biol, 50(5):942-52 (2014).
Wagner, C. C., et al., Positron emission tomography for use in microdosing studies. Curr Opin Drug Discov Devel. 11(1):104-10 (2008).
Wang, C. et al., The psoriasis-associated D10N variant of the adaptor Act1 with impaired regulation by the molecular chaperone hsp90, Nat Immunol, 14(1):72-81 (2013).
Weber, W. A., et al., Technology Insight: novel imaging of molecular targets is an emerging area crucial to the development of targeted drugs. Nat Clin Pract Oncol. 5(1):44-54 (2008).
Workman, P. et al., Drugging the cancer chaperone HSP90: combinatorial therapeutic exploitation of oncogene addiction and tumor stress. Ann N Y Acad Sci. 1113:202-216 (2007).
Workman, P. et al., Minimally invasive pharmacokinetic and pharmacodynamics technologies in hypothesis-testing clinical trials of innovative therapies, J. Natl. Cancer Inst. 98(9):580-598 (2006).
Written Opinion for PCT/US2015/50753, 7 pages (dated Dec. 18, 2015).

* cited by examiner

HSP90-TARGETED INFLAMMATION AND INFECTION IMAGING AND THERAPY

CROSS REFERENCE TO RELATED APPLICATIONS

This application claims priority to U.S. Provisional Application 62/051,590 filed on Sep. 17, 2014, which is incorporated herein by reference in its entirety.

BACKGROUND OF THE INVENTION

Inflammation is part of the complex biological response of vascular tissues to harmful stimuli, such as pathogens, damaged cells, or irritants. The classical signs of acute inflammation are pain, heat, redness, swelling, and loss of function. Inflammation is a protective attempt by the organism to remove the injurious stimuli and to initiate the healing process. In an inflammatory response, cytokines and chemokines are released from various cell types, which increases blood vessel permeability, upregulates endothelial receptors, and increases egress of various cells of the innate and adaptive immune system to enter surrounding tissue. In autoimmune diseases, the immune system triggers an inflammatory response when there are no harmful stimuli, thus causing damages to normal tissues.

Inflammation can be a localized reaction of live tissue due to an injury, which may be caused by various endogenous and exogenous factors. The exogenous factors include physical, chemical, and biological factors. The endogenous factors include inflammatory mediators, antigens, and antibodies. Endogenous factors often develop under the influence of an exogenous damage. An inflammatory reaction is often followed by an altered structure and penetrability of the cellular membrane. Endogenous factors, namely, mediators, antigens, and autogens define the nature and type of an inflammatory reaction, especially its course in the zone of injury. In the case where tissue damage is limited to the creation of mediators, an acute form of inflammation develops. If immunologic reactions are also involved in the process, through the interaction of antigens, antibodies, and autoantigens, a long-term inflammatory process will develop. Various exogenous agents, for example, infection, injury, radiation, also further the course of inflammatory process on a molecular level by damaging cellular membranes which initiate biochemical reactions.

Infection is the invasion of a host organism's body tissues by disease-causing agents, their multiplication, and the reaction of host tissues to these organisms and the toxins they produce. The disease-causing agents can be infectious agents such as viruses, viroids, and prions, microorganisms such as bacteria, nematodes such as roundworms and pinworms, arthropods such as ticks, mites, fleas, and lice, fungi such as ringworm, or macroparasites such as tapeworms. Symptoms of an infection can be signs affecting the whole body, such as fatigue, loss of appetite, weight loss, fevers, night sweats, chills, aches and pains, or signs specific to individual body parts, such as skin rashes, coughing, or a runny nose. Hosts can fight infections using their immune system. Mammalian hosts react to infections with an innate response, often involving inflammation, followed by an adaptive response. Infections can cause host tissue damage. In certain cases, the host's protective immune mechanisms are compromised, and the organism inflicts damage on the host. In some cases, microorganisms cause tissue damage by releasing a variety of toxins or destructive enzymes.

Targeted imaging for targeted therapy—using radiolabeled forms of targeted therapeutic agents for PET imaging—is much advocated for the future of medical imaging & drug development, by the National Cancer Institute and others. (National Cancer Institute, U.S. National Institutes of Health. A workshop regarding what in-vivo molecular imaging probes are needed to support future translational studies in cancer therapeutics. Paper presented at: Strategies for Imaging Priority Targets, 2002; Frankfurt, Germany; Weber W A et al. Nat Clin Pract Oncol. 2008; 5(1):44-54; Workman P et al. J Natl Cancer Inst. 2006; 98(9):580-598; Workman P et al. Ann N Y Acad Sci. 2007; 1113:202-216). The unique potential of PET microdose studies in development of drugs as therapeutic and/or diagnostic imaging agents is recognized by the US FDA and others. A review of published PET micro-dosing studies is provided by Wagner et al (Wagner C C et al. Curr Opin Drug Discov Devel. 2008 January; 11(1):104-10).

Various agents for infection and/or inflammation imaging are currently in clinical use (Petruzzi et al. Semin. Nucl. Med. 2009; 39(2): 115-123). However, more imaging agents will provide additional options for imaging, diagnostics, and treatment of infection and/or inflammation.

SUMMARY OF THE INVENTION

The present invention, among other things, encompasses the recognition that Hsp90 plays a role in mediating inflammation and/or infection (see e.g., "The psoriasis-associated D10N variant of the adaptor Act1 with impaired regulation by the molecular chaperone hsp90," 2013; Nat. Immunol. 14(1):72-81), and that further understanding the role of Hsp90 in inflammation and infection can be valuable in the diagnosis and treatment of inflammation and/or infection. In some embodiments, the present invention solves certain problems associated with conventional imaging of a tissue affected by an inflammation and/or infection. In some embodiments, the present invention provides methods for non-invasive imaging of inflammation and/or infection. In certain embodiments, the present invention provides novel methods for monitoring, diagnosis, and treatment of an inflammation and/or infection. In some embodiments, provided methods comprise imaging an inflammation and/or infection using labeled compounds that bind to Hsp90, and/or labeled compounds having the structure of any of formula I to IX. In some embodiments, provided methods comprise imaging an inflammation and/or infection using labeled compounds that bind to Hsp90, and/or labeled compounds having the structure of formula I. In some embodiments, the invention provides a method for detecting and treating an inflammation and/or infection, wherein higher uptake of the Hsp90-targeted imaging agent indicates more likelihood for the subject to benefit from Hsp90 inhibitor therapy.

In some embodiments, the present invention provides a method of imaging a tissue affected by an inflammation and/or infection in a subject in need thereof, comprising steps of: (a) administering to the subject a labeled compound that binds to Hsp90; and (b) imaging the tissue by detecting the labeled compound in the subject.

In some embodiments, the present invention provides a method for imaging a tissue affected by an inflammation and/or infection in a subject in need thereof, comprising steps of: (a) administering to the subject a labeled compound of any of formula I to IX as described herein; and (b) imaging the tissue by detecting the labeled compound in the subject.

In some embodiments, the present invention provides a method for imaging a tissue affected by an inflammation and/or infection in a subject in need thereof, comprising steps of:
(a) administering to the subject a labeled compound of formula I:

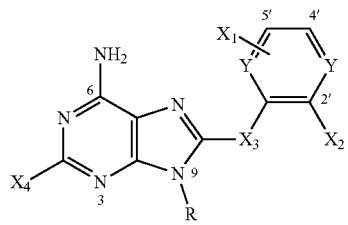

or its pharmaceutically acceptable salt thereof, wherein each of Y, R, $X_1$, $X_2$, $X_3$, and $X_4$ is a defined herein; wherein each hydrogen is optionally and independently substituted with a group that can be detected by a medical imaging technique, and/or at least one atom in the compound is optionally enriched in an isotope that can be detected by a medical imaging technique; and
(b) imaging the tissue by detecting the labeled compound in the subject.

In some embodiments, the present invention provides a method for the diagnosis of a tissue affected by an inflammation and/or infection, comprising steps of:
(a) administering a compound of any of formula I to IX to a subject in need thereof; and
(b) imaging the tissue by detecting the labeled compound in the subject.

In some embodiments, the present invention provides a method for the treatment of a tissue affected by, or prevention of a tissue from, an inflammation and/or infection, comprising steps of:
(a) administering a compound of any of formula I to IX to a subject in need thereof; and
(b) imaging the tissue by detecting the labeled compound in the subject.

In some embodiments, the present invention provides a method for monitoring the effect of an inflammation and/or infection treatment in a subject in need thereof, comprising steps of:
(a) administering a labeled compound of any of formula I to IX to the subject who is scheduled for the inflammation and/or infection treatment, currently undergoing the inflammation and/or infection treatment, or has completed or discontinued the inflammation and/or infection treatment;
(b) imaging a tissue affected by the inflammation and/or infection by detecting the labeled compound; and
(c) recommending to the subject an appropriate avoidance, continuation, modification, or termination in the inflammation and/or infection treatment.

In some embodiments, the present invention provides a method for monitoring an inflammation and/or infection treatment regimen, comprising steps of:
(a) administering a labeled compound of any of formula I to IX to a subject under the inflammation and/or infection treatment regimen;
(b) imaging a tissue affected by the inflammation and/or infection by detecting the labeled compound in the subject;
(c) analyzing the images from step (b); and
(d) maintaining, modifying or discontinuing the inflammation and/or infection treatment regimen.

In some embodiments, the present invention provides a method for selecting subjects for an inflammation and/or infection treatment, comprising steps of:
(a) administering a labeled compound of any of formula I to IX to a subject;
(b) imaging a tissue affected by the inflammation and/or infection by detecting the labeled compound in the subject;
(c) analyzing the images from step (b); and
(d) including or excluding the subject for the treatment.

In some embodiments, the present invention provides a method for selecting subjects for an inflammation and/or infection treatment, comprising steps of:
(a) administering to a subject a labeled compound that binds to stress-specific Hsp90; and
(b) imaging a tissue affected by the inflammation and/or infection by detecting the labeled compound in the subject;
wherein increased uptake of the labeled compound indicates more likelihood for the subject to benefit from the treatment.

In some embodiments, the present invention provides a method for determining the dosage of a drug for the treatment of an inflammation and/or infection, comprising steps of:
(a) administering a labeled compound of any of formula I to IX to a subject;
(b) imaging a tissue affected by the inflammation and/or infection by detecting the labeled compound in the subject;
(c) analyzing the images from step (b); and
(d) administering to the subject a suitable amount of the drug.

DEFINITIONS

Figure 1:
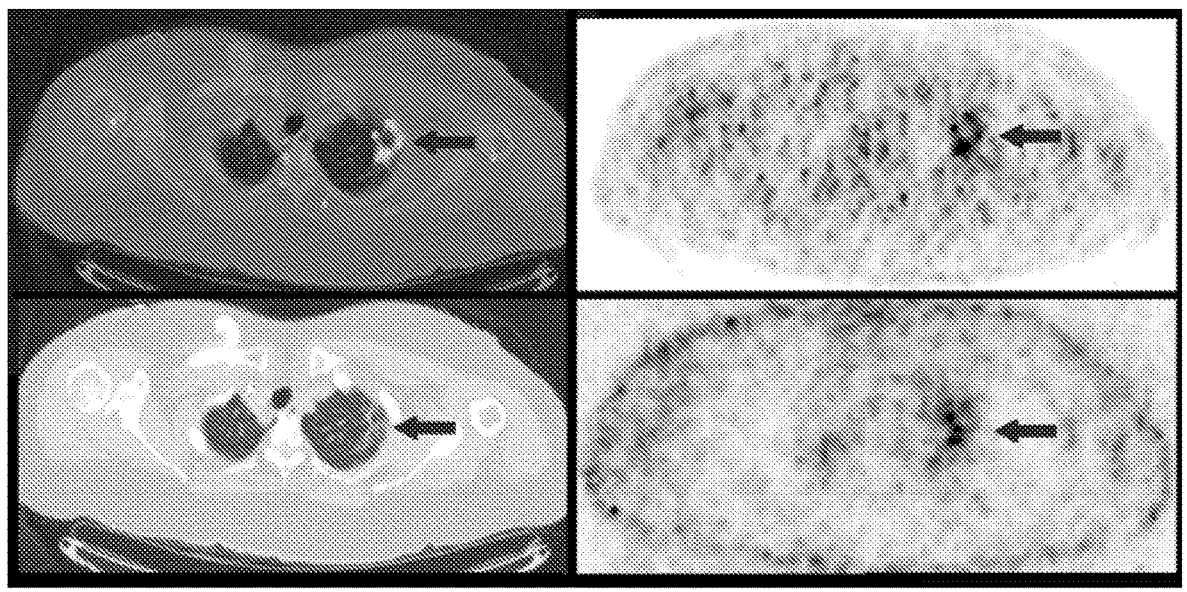
FIG. 1: I-124 PUH71 PET-CT of a chronic pulmonary infiltrate in a 59 year old woman with ovarian cancer. Shown are I-124 PUH71 PET-CT images of a single transaxial plane through the chest, showing distinct accumulation of I-124 PUH71 in an inflammatory pulmonary infiltrate (arrows) in the apex of the patient's left lung. PET-CT imaging was performed 24 hours after intravenous injection of 9.3 mCi I-124 PUH71. Shown are I-124 PUH71 PET images with and without attenuation correction (top right and bottom right, respectively); companion CT (bottom left); and fusion I-124 PUH71 PET-CT (top left).
Figure 2:
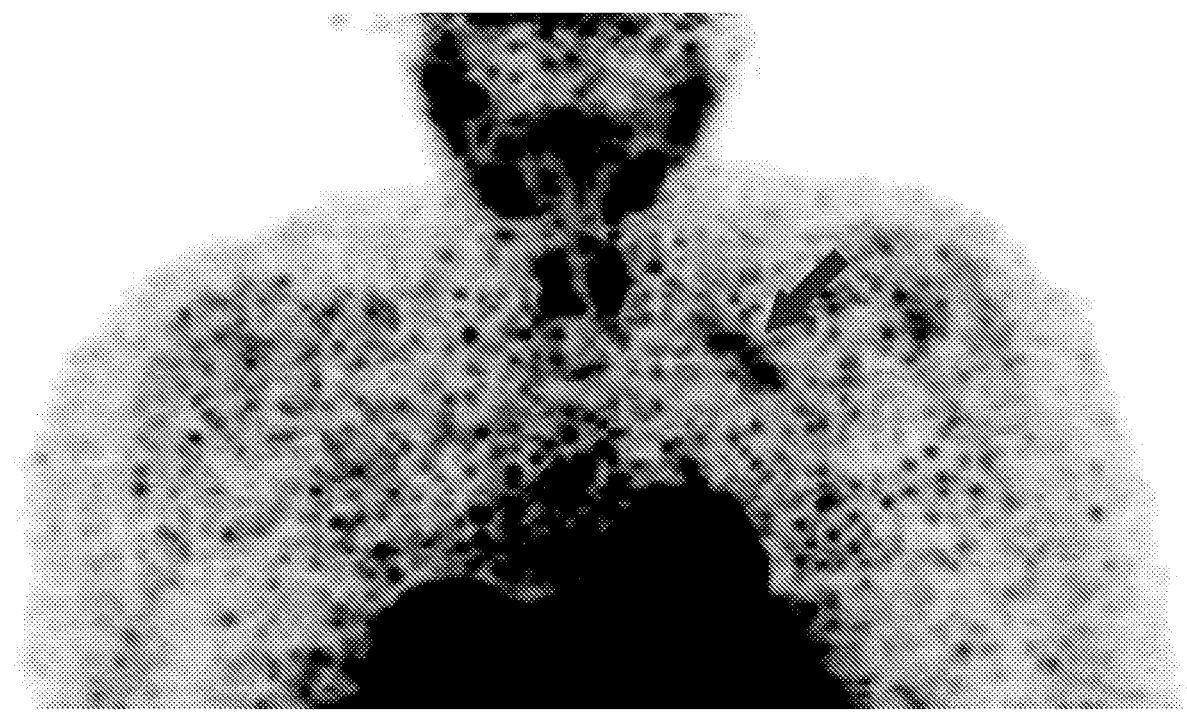
FIG. 2: I-124 PUH71 PET-CT of a chronic pulmonary infiltrate in a 59 year old woman with ovarian cancer. Shown is a 3-dimensional maximum intensity projection (MIP) PET image of a portion of the patient's body, spanning from the skull base to the lower chest region. The PET image shows distinct accumulation of I-124 PUH71 in an inflammatory pulmonary infiltrate (arrow) in the apex of the patient's left lung. PET-CT imaging was performed 24 hours after intravenous injection of 9.3 mCi I-124 PUH71.

Certain compounds of the present disclosure, and definitions of specific functional groups are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

As used herein, the following definitions shall apply unless otherwise indicated.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic, bicyclic or polycyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-12 aliphatic carbon atoms. In some embodiments, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR' (as in N-substituted pyrrolidinyl)).

The term "unsaturated," as used herein, means that a moiety has one or more units of unsaturation.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent.

The term "alkynylene" refers to a bivalent alkynyl group. A substituted alkynylene chain is a polymethylene group containing at least one double bond in which one or more hydrogen atoms are replaced with a substituent.

The term "acyl," used alone or a part of a larger moiety, refers to groups formed by removing a hydroxy group from a carboxylic acid.

The term "halogen" means F, Cl, Br, or I.

The terms "aralkyl" and "arylalkyl" are used interchangeably and refer to alkyl groups in which a hydrogen atom has been replaced with an aryl group. Such groups include, without limitation, benzyl, cinnamyl, and dihydrocinnamyl.

The term "aryl" used alone or as part of a larger moiety as in "aralkyl," "aralkoxy," or "aryloxyalkyl," refers to monocyclic, bicyclic or polycyclic ring systems having a total of five to fourteen ring members, wherein at least one ring in the system is aromatic and wherein each ring in the system contains 3 to 7 ring members. The term "aryl" may be used interchangeably with the term "aryl ring."

In certain embodiments of the present disclosure, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 14 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The terms "heteroaralkyl" and "heteroarylalkyl" refer to an alkyl group substituted by a heteroaryl moiety, wherein the alkyl and heteroaryl portions independently are optionally substituted.

The term "heteroaliphatic," as used herein, means aliphatic groups wherein one or more carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "heterocyclyl," "heterocycloaliphatic," or "heterocyclic" groups.

As used herein, the terms "heterocycle," "heterocyclyl," "heterocyclic radical," "heterocyclic group," "heterocyclic moiety," and "heterocyclic ring" are used interchangeably and refer to a stable 3- to 14-membered monocyclic or 7-14-membered bicyclic or polycyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The term "heterocycle" also includes groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As used herein and in the claims, the singular forms "a", "an", and "the" include the plural reference unless the context clearly indicates otherwise. Thus, for example, a reference to "a compound" includes a plurality of such compounds.

In another aspect, the present disclosure provides "pharmaceutically acceptable" compositions, which comprise a therapeutically effective amount of one or more of the compounds described herein, formulated together with one or more pharmaceutically acceptable carriers (additives) and/or diluents. As described in detail, the pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Unless otherwise stated, structures depicted herein are also meant to include all isomeric (e.g., enantiomeric, diastereomeric, and geometric (or conformational)) forms of the structure; for example, the R and S configurations for each stereocenter, Z and E double bond isomers, and Z and E conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure.

Provided compounds may comprise one or more saccharide moieties. Unless otherwise specified, both D- and L-configurations, and mixtures thereof, are within the scope of the disclosure. Unless otherwise specified, both α- and β-linked embodiments, and mixtures thereof, are contemplated by the present disclosure.

If, for instance, a particular enantiomer of a compound of the present disclosure is desired, it may be prepared by asymmetric synthesis, chiral chromatography, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this disclosure. Such compounds are useful, for example, as analytical tools, as probes in biological assays, or as therapeutic agents in accordance with the present disclosure.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-(CH_2)_{0-4}SR^\circ$; $-(CH_2)_{0-4}S(O)R^\circ$; $-(CH_2)_{0-4}S(O)_2R^\circ$; $-O-(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O-(CH_2)_{0-1}$pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR^\circ$; $-SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $-PR^\circ_2$; $-OPR^\circ_2$; $-SiR^\circ_3$; $-OSiR^\circ_3$; $-(C_{1-4}$ straight or branched)alkylene)O$-N(R^\circ)_2$; or $-(C_{1-4}$ straight or branched)alkylene)C(O)O$-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6-membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(halo$R^\bullet$), $-(CH_2)_{0-2}OH$, $-(CH_2)_{0-2}OR^\bullet$, $-(CH_2)_{0-2}CH(OR^\bullet)_2$; $-O$(halo$R^\bullet$), $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)C(O)O$R^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, -(halo$R^\bullet$), $-OH$, $-OR^\bullet$, $-O$(halo$R^\bullet$), $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)$ R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "labeled compound" refers to a compound that produces an enhanced signal compared to the compound prior to labeling when detected by a medical imaging technique. A labeled compound may have one or more "labels", which is an atom or moiety that leads to an enhanced signal. In some embodiments, a labeled compound is radiolabelled, wherein the labeled compound contains one or more enriched radioactive isotopes of at least one element. Exemplary suitable isotopes include but are not limited to those used in positron emission tomography (PET), such as $^{124}$I, $^{11}$C, $^{15}$O, $^{13}$N, and $^{18}$F; and those used in single-photon emission computed tomography (SPECT). In some embodiments, a labeled compound is labeled with one or more non-radioactive labels. In some embodiments, a non-radioactive label can be detected by Magnetic Resonance Imaging (MRI). In some embodiments, the non-radioactive label is $^{19}$F. In some embodiments, a label is suited for MRI. In some embodiments, the label is a contrast agent. Many methods are known in the art for compound labeling. In some embodiments, a compound is labeled by substituting a hydrogen atom with a label. In some embodiments, a compound is labeled by substituting a hydrogen atom with a suitable fluorine or iodine label. In some embodiments, a suitable fluorine label is $^{18}$F. In some embodiments, a suitable fluorine label is $^{19}$F. In some embodiments, a suitable iodine label is $^{123}$I. In some embodiments, a suitable iodine label is $^{124}$I. In some embodiments, a suitable iodine label is $^{125}$I. In some embodiments, a suitable iodine label is $^{131}$I. In some embodiments, a label comprises more than one atom. In some other embodiments, a compound is labeled by altering the isotopic composition of one or more atoms, often by increasing the percentage of the isotope(s) that can be detected by the medical imaging technique to be used ("enriched"). In some embodiments, a labeled compound is isotopically enriched in one of $^{123}$I, $^{124}$I, $^{125}$I, $^{131}$I, $^{11}$C, $^{15}$O, $^{13}$N, and $^{18}$F or their combinations thereof. In some embodiments, a labeled compound is isotopically enriched in $^{123}$I. In some embodiments, a labeled compound is isotopically enriched in $^{124}$I. In some embodiments, a labeled compound is isotopically enriched in $^{125}$I. In some embodiments, a labeled compound is isotopically enriched in $^{131}$I. In some embodiments, a labeled compound is isotopically enriched in $^{11}$C. In some embodiments, a labeled compound is isotopically enriched in $^{15}$O. In some embodiments, a labeled compound is isotopically enriched in $^{13}$N. In some embodiments, a labeled compound is isotopically enriched in $^{18}$F. In some embodiments, a labeled compound comprises more than one label. In some embodiments, a labeled compound can be detected by one or more medical imaging techniques, for example but not limited to MRI, PET and SPECT. In some embodiments, a labeled compound comprises more than one radioactive label. In some embodiments, a labeled compound comprises more than one fluorine label. In some embodiments, a labeled compound comprises more than one $^{19}$F. In some embodiments, a label is a fluorophore moiety. In some embodiments, a label is a nanometer-sized agent. In some embodiments, a label is a nanoparticle. In some embodiments, a label is a nanotube. In some embodiments, a label is liposome. In some embodiments, a nanotube or liposome comprises a moiety that produces an enhanced signal. In some embodiments, one or more MRI agents are linked or packaged in a nanotube, nanoparticle or liposome. In some embodiments, one nanometer-sized agent or nanoparticle or liposomal micelle is used to label more than one molecule of a compound to be labeled; for example, more than one molecule of the compound to be labeled can be linked to a single nanoparticle. In some embodiments, a label is covalently linked to a compound. In some embodiments, a label is non-covalently linked to a compound.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "palliative" refers to treatment that is focused on the relief of symptoms of a disease and/or side effects of a therapeutic regimen, but is not curative.

As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

As used herein, an "inflammation" means a disease, disorder, or condition characterized by inflammation of body tissue or having an inflammatory component. These include local inflammatory responses and systemic inflammation. Examples of such inflammatory disorders include: transplant rejection, including skin graft rejection; chronic inflammatory disorders of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung disorders such as asthma, adult respiratory distress syndrome, and chronic obstructive airway disease; inflammatory disorders of the eye including corneal dystrophy, trachoma, onchocerciasis, uveitis, sympathetic ophthalmitis and endophthalmitis; chronic inflammatory disorders of the gums, including gingivitis and periodontitis; tuberculosis; leprosy; inflammatory diseases of the kidney including uremic complications, glomerulonephritis and nephrosis; inflammatory disorders of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune disorders, immune-complex vasculitis, systemic lupus and erythematodes; systemic lupus erythematosus (SLE); and inflammatory diseases of the heart such as cardiomyopathy, ischemic heart disease hypercholesterolemia, atherosclerosis; as well as various other diseases with significant inflammatory components, including preeclampsia; chronic liver failure, brain and spinal cord trauma, and cancer. There may also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent used in cancer chemotherapy. In some embodiments, "treatment of an inflammatory disorder" includes administering a described compound or a composition to a subject who has an inflammatory disorder, a symptom of such a disorder, or a predisposition towards such a disorder, with the purpose to cure, relieve, alter, affect, or prevent the inflammatory disorder, the symptom of it, or the predisposition towards it.

As used herein, an "infection" means a disease, disorder or condition, caused by one or more microorganisms, including but not limited to viruses, bacteria, fungi, and parasites. In some embodiments, the infection is a bacterial infection (e.g., infection by E. coli, Klebsiella pneumoniae, Pseudomonas aeruginosa, Salmonella spp., Staphylococcus aureus, Streptococcus spp., or vancomycin-resistant enterococcus). In certain embodiments, the infection is a fungal infection (e.g., infection by a mould, a yeast, or a higher fungus). In some embodiments, the infection is a parasitic infection (e.g., infection by a single-celled or multicellular parasite, including Giardia duodenalis, Cryptosporidium parvum, Cyclospora cayetanensis, and Toxoplasma gondii). In some embodiments, the infection is a viral infection (e.g., infection by a virus associated with AIDS, avian flu, chickenpox, cold sores, common cold, gastroenteritis, glandular fever, influenza, measles, mumps, pharyngitis, pneumonia, rubella, SARS, and lower or upper respiratory tract infection (e.g., respiratory syncytial virus)).

As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a disease, disorder, and/or condition. In some embodiments, the term "treatment" refers to treatment of an inflammation and/or infection with the anti-inflammatory drugs and/or anti-infection drug provided herein. Treatment may be administered to a subject who does not exhibit signs of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition. Daily usage of a formulation of the present invention will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts. A particular unit dose may or may not contain a therapeutically effective amount of a therapeutic agent.

The expression "unit dose" as used herein refers to a physically discrete unit of a formulation appropriate for a subject to be treated. It will be understood, however, that the total daily usage of a formulation of the present invention will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts. A particular unit dose may or may not contain a therapeutically effective amount of a therapeutic agent.

An individual who is "suffering from" a disease, disorder, and/or condition has been diagnosed with and/or displays one or more symptoms of the disease, disorder, and/or condition.

An individual who is "susceptible to" a disease, disorder, and/or condition has not been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Detailed Description of Certain Embodiments

The present invention encompasses the recognition of the importance to develop new methods for imaging tissue inflammation and/or infection, for the diagnosis, treatment, or prevention of an inflammation and/or infection, for monitoring the effect of an inflammation and/or infection treatment, for selecting subjects for an inflammation and/or infection treatment, and for determining drug dosages. The present invention provides, among other things, novel methods for the aforementioned purposes.

Hsp90 has been found to be associated with inflammation and infection (Barabutis N et al. Am J Physiol Lung Cell Mol Physiol. 2013 Jun. 15; 304(12):L883-93; Bohonowych J E et al. Prostate. 2014 April; 74(4):395-407; Kakeda M et al. J Am Acad Dermatol. 2014 April; 70(4):683-690; Wang C et al. Nat Immunol. 2013 January; 14(1):72-81; Thangjam G S et al. Am J Respir Cell Mol Biol. 2014 May; 50(5): 942-52; Collins C B et al. Inflamm Bowel Dis. 2014 April; 20(4):685-94; Chen D et al. Biochem Biophys Res Commun. 2014 Jan. 3; 443(1):326-32; Shebrain S, Ramjit A. J Surg Res. 2013 November; 185(1):e53-4; Collins C B et al. Mucosal Immunol. 2013 September; 6(5):960-71). While Hsp90 may be related to inflammation and infection, prior to the present disclosure, methods of identifying patients most likely to benefit from Hsp90 therapy in these indications were unknown.

The present invention encompasses the recognition that it is important to be able to define a patient subpopulation that should receive a treatment in order to engender successful development of targeting agents for therapy. Such selection may reduce the number of patients receiving ineffective treatment, as well as minimize the over- or improper use of drug treating infection, which can lead to resistance. In some embodiments, the present invention provides methods of determining whether a patient has an inflammation or infection. In some embodiments, the present invention provides a method of assaying the presence of Hsp90 in an inflammation and/or infection. In some embodiments, the present invention provides a method of assaying an Hsp90-mediated inflammation and/or infection.

As previously described by Applicant in WO2013/009655, the entire contents of which are incorporated herein by reference, "oncogenic Hsp90" is a cell stress-specific form of Hsp90 that is expanded and constitutively maintained in the tumor cell context, and that may execute functions necessary to maintain the malignant phenotype. Without wishing to be bound by any particular theory, the present invention encompasses the recognition that a related form of Hsp90 observed in the tumor context can also be observed in tissue affected by an inflammation and/or infection (i.e., stress-specific Hsp90) using methods provided herein. In such a case, it is believed that tissue affected by an inflammation and/or infection comprising stress-specific Hsp90 has a greater likelihood of benefiting from treatment with Hsp90 inhibitors. In some embodiments, provided methods are useful for detecting and treating an inflammation and/or infection, wherein a higher uptake of an Hsp90-targeting imaging agent indicates a higher likelihood a patient will benefit from Hsp90 inhibitor therapy. The generated imagery depicts affected tissues in the subject as sites of high or low levels of signal from the labeled compound relative to surrounding healthy tissues in the same organ; or alternatively, depicts an organ with diffuse infectious/inflammatory disease as an organ with diffuse, relatively-high or -low level of signal, compared to the level of signal visualized in that organ in other healthy subjects.

A stressed cell, i.e., a cell under stress caused by or associated with inflammation and/or infection, contains a complex mixture of Hsp90 complexes. While a majority of Hsp90 complexes perform "housekeeping" chaperone functions similarly to non-stressed, normal cells, a functionally distinct fraction of Hsp90 buffers the cell's proteome altered in the stress process (i.e., stress-specific Hsp90). "Stress-specific Hsp90" as used herein means a form of Hsp90 expressed in response to inflammation and/or infection. Such stress-specific Hsp90 is the fraction of Hsp90 that is expanded and constitutively maintained in the inflamed and/or infected cell context, and that specifically interacts with inflammation/infection proteins required to cause or maintain an inflamed or infected cell state, aberrant proliferative features, and/or invasive behavior.

Stress-specific Hsp90 manifests in response to the altered proteome that arises in inflamed and/or infected cells, and may differ from housekeeping or other forms of Hsp90 by way of chemical modifications (e.g., post-translational modifications) or biochemical modifications (e.g., co-chaperone and adapter protein recruitment), by way of nonlimiting example. Indeed, different types of cell stress can engender different stress forms of Hsp90. Without wishing to be bound by any particular theory, it is believed that when inflammation and/or infection becomes reliant upon a Hsp90 inflammation/infection proteome, this proteome becomes dependent on "stress-specific Hsp90" for functioning and stability. This symbiotic interdependence suggests that reliance of inflammation and/or infection on an Hsp90 inflammation/infection proteome equals reliance on "stress-specific Hsp90". Measuring the abundance of the latter is a read-out of the first, and therefore, in accordance with the present disclosure, is a biomarker for Hsp90 therapy enrichment. In some embodiments, provided are methods of identifying and measuring the abundance of this stress-specific Hsp90 species in inflammation and/or infection for predicting response to Hsp90 therapy.

The present disclosure encompasses the recognition that certain small molecule compounds selectively interact with stress-specific Hsp90. In some embodiments, a labeled compound as disclosed herein binds to stress-specific Hsp90. In some embodiments, a labeled compound specificially binds to stress-specific Hsp90. In some embodiments, a labeled compound binds to a stress-specific form of Hsp90 selectively over a housekeeping form of Hsp90 (i.e., a form characterized by normal chaperone functions and/or not predominantly expressed in response to tissue stress caused by or associated with inflammation or infection).

In some embodiments, a labeled compound inhibits stress-specific Hsp90. In some embodiments, a labeled compound selectively inhibits stress-specific Hsp90. In some embodiments, a labeled compound inhibits a stress specific form of Hsp90 selectively over a housekeeping form of Hsp90.

In some embodiments, a labeled compound binds to stress-specific Hsp90 selectively over a housekeeping form of Hsp90. In some embodiments, a ratio of binding stress-specific Hsp90 to a housekeeping form of Hsp90 of about 1.5 or greater indicates that an inflammation/infection patient will be susceptible to Hsp90 inhibition therapy. In some embodiments, a ratio of binding stress-specific Hsp90 to a housekeeping form of Hsp90 of about 2 or greater indicates that an inflammation/infection patient will be susceptible to Hsp90 inhibition therapy. In some embodiments, a ratio of binding stress-specific Hsp90 to a housekeeping form of Hsp90 of about 2.5 or greater indicates that an inflammation/infection patient will be susceptible to Hsp90 inhibition therapy. In some embodiments, a ratio of binding stress-specific Hsp90 to a housekeeping form of Hsp90 of about 3 or greater indicates that an inflammation/infection patient will be susceptible to Hsp90 inhibition therapy. In some embodiments, a ratio of binding stress-specific Hsp90 to a housekeeping form of Hsp90 of about 4 or greater indicates that an inflammation/infection patient will be susceptible to Hsp90 inhibition therapy. In some embodiments, a ratio of binding stress-specific Hsp90 to a housekeeping form of Hsp90 of about 5 or greater indicates that an inflammation/infection patient will be susceptible to Hsp90 inhibition therapy.

It will be appreciated that in some embodiments, the methods described herein may be conducted by imaging at the cellular level. This can be advantageous in certain contexts, for example infectious disease of blood cells, where imaging detects signals coming from individuals cells. In some embodiments, such methods further comprise collecting a tissue sample from a subject prior to imaging. In some embodiments, a labeled compound used in such methods comprises a fluorescent label. In some embodiments, the imaging comprises FACS.

In some embodiments, a ratio of binding inflamed/infected cells to normal cells of about 1.5 or greater indicates that an inflammation/infection patient will be susceptible to Hsp90 inhibition therapy. In other embodiments, a ratio of binding inflamed/infected cells to normal cells of about 2 or greater indicates that an inflammation/infection patient will be susceptible to Hsp90 inhibition therapy. In still other embodiments, a ratio of binding inflamed/infected cells to normal cells of about 2.5 or greater indicates that an inflammation/infection patient will be susceptible to Hsp90 inhibition therapy. In still other embodiments, a ratio of binding inflamed/infected cells to normal cells of about 3 or greater indicates that an inflammation/infection patient will be susceptible to Hsp90 inhibition therapy. In still other embodiments, a ratio of binding inflamed/infected cells to normal cells of about 4 or greater indicates that an inflammation/infection patient will be susceptible to Hsp90 inhibition therapy. In still other embodiments, a ratio of binding inflamed/infected cells to normal cells of about 5 or greater indicates that an inflammation/infection patient will be susceptible to Hsp90 inhibition therapy.

It has been found that the labeled compounds that bind to Hsp90 as provided herein have a sustained retention in inflamed/infected tissue. In some embodiments, a labeled compound provided herein has been found to sustain in a lesion after uptake, relative to its clearance from the blood and surrounding healthy tissues. As such, imaging methods using the labeled compound provided herein have a number of advantages, including greater clarity of lesion uptake, higher lesion-to-background ratio, and improved clarity over time of detectable signal.

Figure 3:
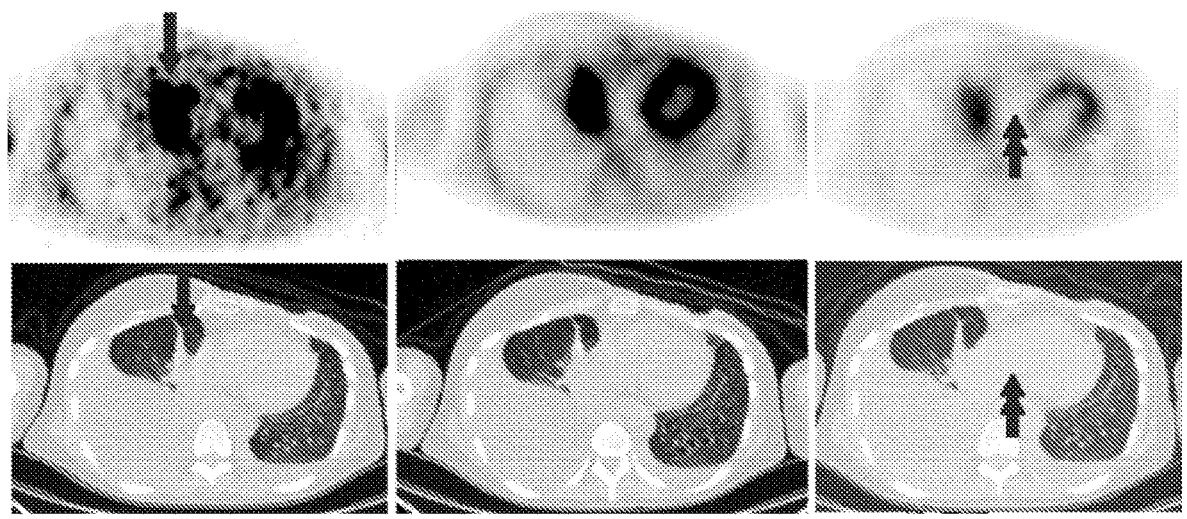
FIGS. 3 and 4: I-124 PUH71 PET-CT of a pulmonary consolidation in a 49 year old woman with breast cancer. Shown are corresponding serial PET and CT images of a single transaxial plane through the patient's chest (FIG. 3), and 3-dimensional maximum intensity projection (MIP) PET images of a portion of the patient's chest (FIG. 4) obtained at three different time-points after a single injection of 6.5 mCi I-124 PUH71 mixed with a therapeutic dose of 35 mg non-radioactive PUH71: immediately (left column), 4 hours (middle column) and 24 hours (right column), post-injection. PET image intensity at all time points is scaled by the same window settings (upper threshold: 5.00 kBq/mL, lower threshold: 0.00 kBq/mL). An inflammatory pulmonary consolidation in the right lung (arrow) demonstrates distinct accumulation and sustained retention of I-124 PUH71 at all time points, after tracer has cleared from blood stream (double arrow points at void of activity within the cardiac atrium; distinct tracer retention in adjacent left ventricle myocardium also visualized). Patient had a large right pleural effusion (arrowhead). In addition to receiving an ongoing therapeutic regimen of PUH71 (three week cycles of 35 mg twice a week for two weeks, then no dose for one week), the patient received antibiotic treatment and pleural fluid drainage. Two weeks after these images were taken, a CT scan showed the pulmonary consolidation had resolved.
Figure 4:

The present invention encompasses the recognition that methods for detecting the existence and location of an infection or inflammation are useful in a clinical setting for the timely diagnosis and treatment of infection or inflammation. This is particularly the case when infection or inflammation resides in an internal tissue. In some embodiments, the present invention is useful in this context and can be used to detect inflammation and/or infection at an earlier stage than other methods. In some embodiments, provided methods are used to detect inflammation and/or infection at less than about 12 hours, 11 hours, 10 hours, 9 hours, 8 hours, 7 hours, 6 hours, 5 hours, 4 hours, 3 hours, 2 hours, or 1 hour post-administration of a labeled compound. In some embodiments, provided methods allow for same-day diagnosis of an inflammation and/or infection. As shown by FIGS. 3 and 4, using labeled PUH71 as a radiotracer, an inflammation/infection can be detected in about 4 hours after the injection of the radiotracer. Without wishing to be bound by any theory, this advantage of early detection is contributed to not only by PUH71's high uptake relative to surrounding healthy tissues and its sustained retention in the diseased tissue, but also its rapid blood clearance.

It will be appreciated that in other contexts, imaging or reimaging inflammation and/or infection at later timepoints w/o additional administration of labeled compound is advantageous. For example, a clinician may desire to obtain additional scans for confirmation or clarification of prior scans, or to monitor treatment efficacy. In some embodiments, provided methods are used to detect inflammation and/or infection at more than about 12 hours, 15 hours, 18 hours, 20 hours, 24 hours, 36 hours, 48 hours, 72 hours, 96 hours, a week, or more after injection of a labeled compound. As shown by FIGS. 1-4, using labeled PUH71 as a radiotracer, an inflammation/infection can be detected at least about 24 hours after the injection of the radiotracer.

In some embodiments, the present invention provides a method of imaging a tissue affected by inflammation and/or infection in a subject in need thereof, comprising steps of:
    (a) administering to the subject a labeled compound that binds to Hsp90; and
    (b) imaging the tissue by detecting the labeled compound in the subject.

Compounds that bind to Hsp90 and methods of labeling the same are known in the art and familiar to the skilled artisan. Non-limiting examples of compounds that bind to Hsp90 and may be labeled are described by Taldone et al, Expert Opin Ther Pat, 24(5): 501-18 (2014), the entire contents of which are hereby incorporated by reference.

In some embodiments, the method further comprises detecting the presence of the inflammation and/or infection in the tissue by analyzing the image obtained in step (b).

In some embodiments, the present invention provide a method for imaging a tissue affected by an inflammation and/or infection in a subject in need thereof, comprising steps of:
    (a) administering to the subject a labeled compound of any of formula I to IX as described in the specification; and
    (b) imaging the tissue by detecting the labeled compound in the subject.

In some embodiments, the method further comprises detecting the presence of the inflammation and/or infection in the tissue by analyzing the image obtained in step (b).

In some embodiments, the present invention provides a method of imaging a tissue affected by an inflammation and/or infection in a subject in need thereof, comprising steps of:
    (a) administering to the subject an effective amount of a labeled compound of formula I:

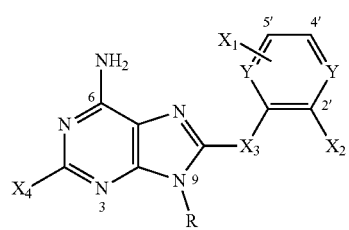

I or its pharmaceutically acceptable salt thereof, wherein:
each Y is independently CH or N;
R is hydrogen, a $C_1$ to $C_{10}$ alkyl, alkenyl, alkynyl, or an alkoxyalkyl group, optionally comprising one or more heteroatoms, or a targeting moiety connected to N9 via a linker;
$X_4$ is hydrogen or halogen;
$X_3$ is $CH_2$, $CF_2$, S, SO, $SO_2$, O, NH, or $NR^2$, wherein $R^2$ is alkyl;
$X_2$ is halogen, alkyl, alkoxy, halogenated alkoxy, hydroxyalkyl, pyrollyl, optionally substituted aryloxy, alkylamino, dialkylamino, carbamyl, amido, alkylamido, dialkylamido, acylamino, alkylsulfonylamino, trihalomethoxy, trihalocarbon, thioalkyl, C(O)O-alkyl, $NH_2$, OH, CN, $SO_2X_5$, $NO_2$, NO, C(S)R, $NHSO_2X_5$, or C(O)R, where $X_5$ is F, $NH_2$, alkyl, or H, and $R_2$ is alkyl, $NH_2$, NH-alkyl, or O-alkyl; and
$X_1$ represents two substituents, which may be the same or different, disposed in the 4' and 5' positions on the aryl group, wherein $X_1$ is selected from halogen, alkyl, alkoxy, halogenated alkoxy, hydroxyalkyl, pyrollyl, optionally substituted aryloxy, alkylamino, dialkylamino, carbamyl, amido, alkylamido, dialkylamido, acylamino, alkylsulfonylamido, trihalomethoxy, trihalocarbon, thioalkyl, COO-alkyl, $NH_2OH$, CN, $SO_2X_5$, $NO_2$, NO, C(S)R, $NHSO_2X_5$, or C(O)$R_2$, where $X_5$ is F, $NH_2$, alkyl, or H, and $R_2$ is alkyl, $NH_2$, NH-alkyl, or O-alkyl, $C_1$ to $C_6$ alkyl or alkoxy, or wherein $X_1$ has the formula —O—$(CH_2)_n$—O—, wherein n is an integer from 1 to 2, and one of the oxygens is bonded at the 5'-position and the other at the 4'-position of the aryl ring; and
(b) imaging the tissue by detecting the labeled compound in the subject.

In some embodiments of a labeled compound of formula I, each hydrogen is optionally and independently substituted with a group that can be detected by a medical imaging technique, and/or at least one atom is optionally enriched in an isotope that can be detected by a medical imaging technique.

In some embodiments, a labeled compound of formula I is a labeled compound having the structure of formula II,

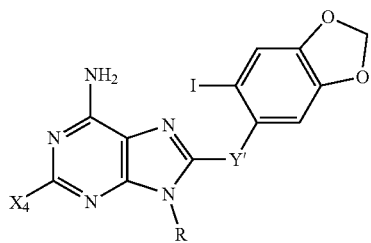

II wherein Y' is —$CH_2$— or S;
$X_4$ is hydrogen or halogen; and R is an amino alkyl moiety, optionally substituted on the amino nitrogen with one or two carbon-containing substituents selected independently from the group consisting of alkyl, alkenyl, and alkynyl substituents, wherein the total number of carbons in the amino alkyl moiety is from 1 to 9.

In some embodiments, the present invention provides a method of imaging a tissue affected by an inflammation and/or infection in a subject in need thereof, comprising steps of:

(a) administering to the subject an effective amount of a labeled compound of formula III or IV:

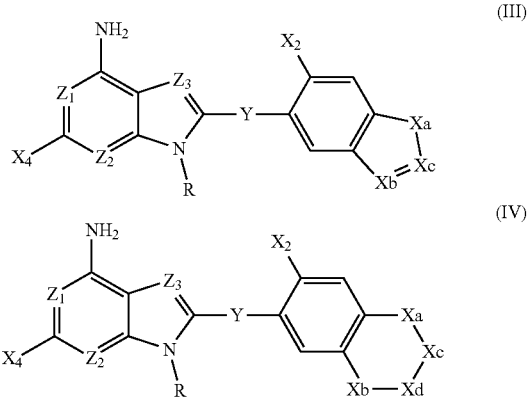

or a pharmaceutically acceptable salt thereof, wherein:
(a) each of $Z_1$, $Z_2$ and $Z_3$ is independently CH or N;
(b) Y is $CH_2$, O, or S;
(c) Xa, Xb, Xc, and Xd are independently selected from CH, $CH_2$, O, N, NH, S, carbonyl, fluoromethylene, and difluoromethylene selected so as to satisfy valence, wherein each bond to an X group is either a single bond or a double bond;
(d) $X_2$ is $^{123}I$, $^{124}I$, $^{125}I$, or $^{131}I$;
(e) $X_4$ is hydrogen or halogen; and
(f) R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl, wherein the R group is optionally interrupted by —S(O)N($R_A$)—, —$NR_A$S(O)—, —$SO_2$N($R_A$)—, —$NR_A$$SO_2$—, —C(O)N($R_A$)—, or —$NR_A$C(O)—, and/or the R group is optionally terminated by —S(O)$NR_AR_B$, —$NR_A$S(O)$R_B$, —$SO_2NR_AR_B$, —$NR_A$$SO_2R_B$, —C(O)$NR_AR_B$, or —$NR_A$C(O)$R_B$, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; and
(b) imaging the tissue by detecting the labeled compound in the subject.

In some embodiments, the present invention provides a method of imaging a tissue affected by an inflammation and/or infection in a subject in need thereof, comprising steps of:

(a) administering to the subject an effective amount of a labeled compound of formula III or IV:

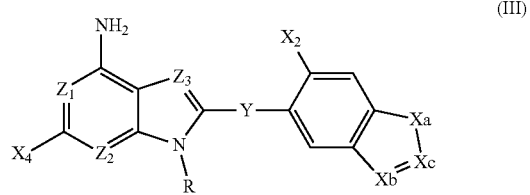

-continued

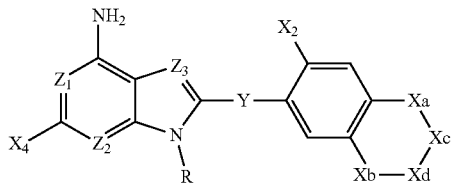
(IV)

or a pharmaceutically acceptable salt thereof, wherein:
(a) each of $Z_1$, $Z_2$ and $Z_3$ is independently CH or N;
(b) Y is $CH_2$, O, or S;
(c) Xa, Xb, Xc, and Xd are independently selected from CH, $CH_2$, O, N, NH, S, carbonyl, fluoromethylene, and difluoromethylene selected so as to satisfy valence, wherein each bond to an X group is either a single bond or a double bond;
(d) $X_2$ is $^{123}I$, $^{124}I$, $^{125}I$, or $^{131}I$;
(e) $X_4$ is hydrogen or halogen; and
(f) R is —$(CH_2)_m$—N—$R_{10}R_{11}R_{12}$ or —$(CH_2)_m$—N—$R_{10}R_{11}$, where m is 2 or 3 and where $R_{10}$-$R_{12}$ are independently selected from hydrogen, methyl, ethyl, ethenyl, ethynyl, propyl, hydroxyalkyl, isopropyl, t-butyl, isobutyl, cyclopentyl, a 3-membered ring including the nitrogen, or a 6-membered ring including the nitrogen and optionally an additional heteroatom with substituents to satisfy valence, with the proviso that when all of $R_{10}$-$R_{12}$ are present the compound further comprises a pharmaceutically acceptable counter ion; and
(b) imaging the tissue by detecting the labeled compound in the subject.

In some embodiments, the present invention provides a method of imaging a tissue affected by an inflammation and/or infection in a subject in need thereof, comprising steps of:
(a) administering to the subject an effective amount of a labeled compound of formula V:

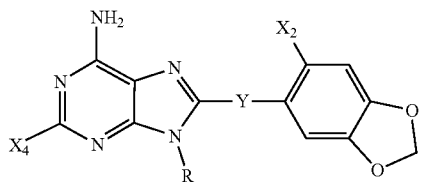
(V)

or a pharmaceutically acceptable salt thereof, wherein:
Y is $CH_2$ or S;
$X_4$ is H or halogen
$X_2$ is $^{123}I$, $^{124}I$, $^{125}I$, or $^{131}I$; and
R is —$(CH_2)_m$—N—$R_{10}R_{11}R_{12}$ or —$(CH_2)_m$—N—$R_{10}R_{11}$, where m is 2 or 3 and where $R_{10}$-$R_{12}$ are independently selected from hydrogen, methyl, ethyl, ethenyl, ethynyl, propyl, hydroxyalkyl, isopropyl, t-butyl, isobutyl, cyclopentyl, a 3-membered ring including the nitrogen, or a 6-membered ring including the nitrogen and optionally an additional heteroatom with substituents to satisfy valence, with the proviso that when all of $R_{10}$-$R_{12}$ are present the compound further comprises a pharmaceutically acceptable counter ion; and
(b) imaging the tissue by detecting the labeled compound in the subject.

In some embodiments, the present invention provides a method of imaging a tissue affected by an inflammation and/or infection in a subject in need thereof, comprising steps of:
(a) administering to the subject an effective amount of a labeled compound of formula VI:

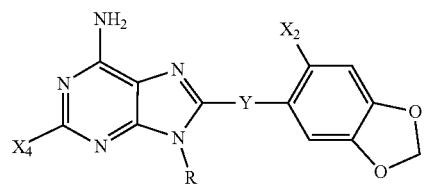
(VI)

or a pharmaceutically acceptable salt thereof, wherein:
Y is $CH_2$ or S;
$X_4$ is H or halogen;
$X_2$ is $^{123}I$, $^{124}I$, $^{125}I$, or $^{131}I$; and
R is 2-ethanesulfonic acid isopropylamide, 2-ethanesulfonic acid ethylamide, 2-ethanesulfonic acid methylamide, 2-ethanesulfonic acid amide, 2-ethanesulfonic acid t-butylamide, 2-ethanesulfonic acid isobutylamide, 2-ethanesulfonic acid cyclopropylamide, isopropanesulfonic acid 2-ethylamide, ethanesulfonic acid 2-ethylamide, N-2 ethyl methanesulfonamide, 2-methylpropane-2-sulfonic acid 2-ethylamide, 2-methylpropane-2-sulfinic acid 2-ethylamide, 2-methylpropane-1-sulfonic acid 2-ethylamide, cyclopropanesufonic acid 2-ethylamide, 3-propane-1-sulfonic acid isopropylamide, 3-propane-1-sulfonic acid ethylamide, 3-propane-1-sulfonic acid methylamide, 3-propane-1-sulfonic acid amide, 3-propane-1-sulfonic acid t-butylamide, 3-propane-1-sulfonic acid isobutylamide, 3-propane-1-sulfonic acid cyclopropylamide, propane-2-sulfonic acid 3-propylamide, ethanesulfonic acid 3-propylamide, N-3-propyl methanesulfonamide, 2-methyl-propane-2-sulfonic acid 3-propylamide, 2-methyl-propane-2-sulfinic acid 3-propylamide, 2-methyl-propane-1-sulfonic acid 3-propylamide, cyclopropanesulfonic acid 3-propylamide, 3-N-isopropyl propionamide, 3-N-ethyl propionamide, 3-N-methyl propionamide, 3-propionamide, 3-N-t-butyl propionamide, 3-N-isobutyl propionamide, 3-N-cyclopropyl propionamide, N-2-ethyl isobutyramide, N-2-ethyl propionamide, N-2-ethyl acetamide, N-2-ethyl formamide, N-2-ethyl 2,2-dimethyl-propionamide, N-2-ethyl 3-methylbutyramide, or cyclopropane carboxylic acid 2-ethyl-amide; and
(b) imaging the tissue by detecting the labeled compound in the subject.

In some embodiments, the present invention provide a method of imaging a tissue affected by an inflammation and/or infection in a subject in need thereof, comprising steps of:
(a) administering to the subject an effective amount of a labeled compound of formula VII:

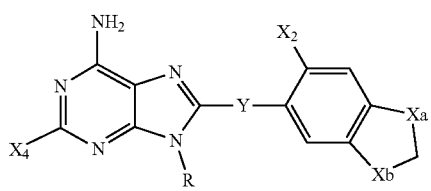

(VII)

or a pharmaceutically acceptable salt thereof, wherein:
one of Xa and Xb is O and the other is $CH_2$;
Y is $CH_2$ or S;
$X_4$ is hydrogen or halogen; and
$X_2$ is $^{123}I$, $^{124}I$, $^{125}I$, or $^{131}I$; and
R is 2-ethanesulfonic acid isopropylamide, 2-ethanesulfonic acid ethylamide, 2-ethanesulfonic acid methylamide, 2-ethanesulfonic acid amide, 2-ethanesulfonic acid t-butylamide, 2-ethanesulfonic acid isobutylamide, 2-ethanesulfonic acid cyclopropylamide, isopropanesulfonic acid 2-ethylamide, ethanesulfonic acid 2-ethylamide, N-2 ethyl methanesulfonamide, 2-methyl-propane-2-sulfonic acid 2-ethylamide, 2-methyl-propane-2-sulfinic acid 2-ethylamide, 2-methyl-propane-1-sulfonic acid 2-ethylamide, cyclopropanesufonic acid 2-ethylamide, 3-propane-1-sulfonic acid isopropylamide, 3-propane-1-sulfonic acid ethylamide, 3-propane-1-sulfonic acid methylamide, 3-propane-1-sulfonic acid amide, 3-propane-1-sulfonic acid t-butylamide, 3-propane-1-sulfonic acid isobutylamide, 3-propane-1-sulfonic acid cyclopropylamide, propane-2-sulfonic acid 3-propylamide, ethanesulfonic acid 3-propylamide, N-3-propyl methanesulfonamide, 2-methyl-propane-2-sulfonic acid 3-propylamide, 2-methyl-propane-2-sulfinic acid 3-propylamide, 2-methyl-propane-1-sulfonic acid 3-propylamide, cyclopropanesulfonic acid 3-propylamide, 3-N-isopropyl propionamide, 3-N-ethyl propionamide, 3-N-methyl propionamide, 3-propionamide, 3-N-t-butyl propionamide, 3-N-isobutyl propionamide, 3-N-cyclopropyl propionamide, N-2-ethyl isobutyramide, N-2-ethyl propionamide, N-2-ethyl acetamide, N-2-ethyl formamide, N-2-ethyl 2,2-dimethyl-propionamide, N-2-ethyl 3-methylbutyramide, or cyclopropane carboxylic acid 2-ethyl-amide; and
(b) imaging the tissue by detecting the labeled compound in the subject.

In some embodiments, the present invention provides a method of imaging a tissue affected by an inflammation and/or infection in a subject in need thereof, comprising steps of:
(a) administering to the subject an effective amount of a labeled compound of formula VIII:

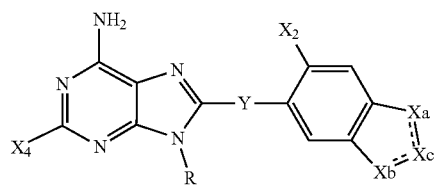

(VIII)

or a pharmaceutically acceptable salt thereof, wherein:
Xa-Xc-Xb is $CH_2$—$CH_2$—$CH_2$, CH=CH—$CH_2$, or $CH_2$—CH=CH;
Y is $CH_2$ or S;
$X_2$ is $^{123}I$, $^{124}I$, $^{125}I$, or $^{131}I$; and
R is 2-ethanesulfonic acid isopropylamide, 2-ethanesulfonic acid ethylamide, 2-ethanesulfonic acid methylamide, 2-ethanesulfonic acid amide, 2-ethanesulfonic acid t-butylamide, 2-ethanesulfonic acid isobutylamide, 2-ethanesulfonic acid cyclopropylamide, isopropanesulfonic acid 2-ethylamide, ethanesulfonic acid 2-ethylamide, N-2 ethyl methanesulfonamide, 2-methyl-propane-2-sulfonic acid 2-ethylamide, 2-methyl-propane-2-sulfinic acid 2-ethylamide, 2-methyl-propane-1-sulfonic acid 2-ethylamide, cyclopropanesufonic acid 2-ethylamide, 3-propane-1-sulfonic acid isopropylamide, 3-propane-1-sulfonic acid ethylamide, 3-propane-1-sulfonic acid methylamide, 3-propane-1-sulfonic acid amide, 3-propane-1-sulfonic acid t-butylamide, 3-propane-1-sulfonic acid isobutylamide, 3-propane-1-sulfonic acid cyclopropylamide, propane-2-sulfonic acid 3-propylamide, ethanesulfonic acid 3-propylamide, N-3-propyl methanesulfonamide, 2-methyl-propane-2-sulfonic acid 3-propylamide, 2-methyl-propane-2-sulfinic acid 3-propylamide, 2-methyl-propane-1-sulfonic acid 3-propylamide, cyclopropanesulfonic acid 3-propylamide, 3-N-isopropyl propionamide, 3-N-ethyl propionamide, 3-N-methyl propionamide, 3-propionamide, 3-N-t-butyl propionamide, 3-N-isobutyl propionamide, 3-N-cyclopropyl propionamide, N-2-ethyl isobutyramide, N-2-ethyl propionamide, N-2-ethyl acetamide, N-2-ethyl formamide, N-2-ethyl 2,2-dimethyl-propionamide, N-2-ethyl 3-methylbutyramide, or cyclopropane carboxylic acid 2-ethyl-amide; and
(b) imaging the tissue by detecting the labeled compound in the subject.

In some embodiments, the present invention provides a method of imaging a tissue affected by an inflammation and/or infection in a subject in need thereof, comprising steps of:
(a) administering to the subject an effective amount of a labeled compound of formula IX:

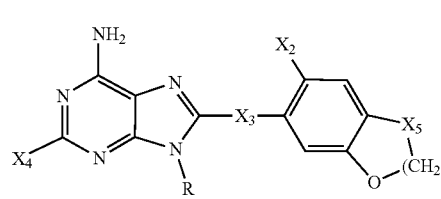

(IX)

or a pharmaceutically acceptable salt thereof, wherein:
$X_3$ is $CH_2$, $CF_2$, S, SO, $SO_2$, O, NH, or $NR^2$, wherein $R^2$ is alkyl;
$X_2$ is $^{123}I$, $^{124}I$, $^{125}I$, or $^{131}I$;
$X_4$ is hydrogen or halogen;
$X_5$ is O or $CH_2$;
R is 3-isopropylaminopropyl, 3-(isopropyl(methyl)amino)propyl, 3-(isopropyl(ethyl)amino)propyl, 3-((2-hydroxyethyl)(isopropyl)amino)propyl, 3-(methyl(prop-2-ynyl)amino)propyl, 3-(allyl(methyl)amino)propyl, 3-(ethyl(methyl)amino)propyl, 3-(cyclopropyl(propyl)amino)propyl, 3-(cyclohexyl(2-hydroxyethyl)amino)propyl, 3-(2-methylaziridin-1-yl)propyl, 3-(piperidin-1-yl)propyl, 3-(4-(2-hydroxyethyl)piperazin-1-yl)propyl, 3-morpholinopropyl, 3-(trimethylammonio)propyl, 2-(isopropylamino)ethyl, 2-(isobutylamino)ethyl, 2-(neopentylamino)ethyl, 2-(cyclopropylmethylamino)ethyl, 2-(ethyl(methyl)amino)ethyl, 2-(isobutyl(methyl)amino)ethyl, or 2-(methyl(prop-2-ynyl)amino)ethyl; and n is 1 or 2;

(b) imaging the tissue by detecting the labeled compound in the subject.

In some embodiments, a compound of formula I binds to Hsp90. In some embodiments, a compound of formula I is an Hsp90 inhibitor. In some embodiments, a compound of formula II binds to Hsp90. In some embodiments, a compound of formula II is an Hsp90 inhibitor. In some embodiments, a compound of formula III binds to Hsp90. In some embodiments, a compound of formula III is an Hsp90 inhibitor. In some embodiments, a compound of formula IV binds to Hsp90. In some embodiments, a compound of formula IV is an Hsp90 inhibitor. In some embodiments, a compound of formula V binds to Hsp90. In some embodiments, a compound of formula V is an Hsp90 inhibitor. In some embodiments, a compound of formula VI binds to Hsp90. In some embodiments, a compound of formula VI is an Hsp90 inhibitor. In some embodiments, a compound of formula VII binds to Hsp90. In some embodiments, a compound of formula VII is an Hsp90 inhibitor. In some embodiments, a compound of formula VIII binds to Hsp90. In some embodiments, a compound of formula VIII is an Hsp90 inhibitor. In some embodiments, a compound of formula IX binds to Hsp90. In some embodiments, a compound of formula IX is an Hsp90 inhibitor.

Hsp90 may have multiple isoforms. In some embodiments, the labeled compound binds to one or more isoforms of Hsp90. In some embodiments, the labeled compound binds to one or more isoforms of Hsp90 expressed in a tissue affected by an inflammation and/or infection. In some embodiments, the labeled compound binds to one form of Hsp90. In some embodiments, the labeled compound binds to more than one form of Hsp90. In some embodiments, the labeled compound binds to more than one form of Hsp90 with comparable affinity. In some embodiments, the labeled compound binds to more than one form of Hsp90 with different affinity.

In some embodiments, Hsp90 is stress-specific Hsp90.

In some embodiments, a labeled compound binds to Hsp90 with a $K_D$ of less than about 1 mM, about 100 µM, about 10 µM or about 1 µM. In some embodiments, a labeled compound binds to Hsp90 with a $K_D$ of less than about 1 mM. In some embodiments, a labeled compound binds to Hsp90 with a $K_D$ of less than about 100 µM. In some embodiments, a labeled compound binds to Hsp90 with a $K_D$ of less than about 10 µM. In some embodiments, a labeled compound binds to Hsp90 with a $K_D$ of less than about 1 µM.

In some embodiments, a labeled compound inhibits Hsp90. In some embodiments, a labeled compound has an $IC_{50}$ of less than about 1 mM, about 100 µM, about 10 µM, about 1 µM, about 100 nM, or about 10 nM. In some embodiments, a labeled compound has an $IC_{50}$ of less than about 1 mM. In some embodiments, a labeled compound has an $IC_{50}$ of less than about 100 µM. In some embodiments, a labeled compound has an $IC_{50}$ of less than about 10 µM. In some embodiments, a labeled compound has an $IC_{50}$ of less than about 1 µM.

In some embodiments, a labeled compound that binds to Hsp90 has the structure of formula I. In some embodiments, a labeled compound that binds to Hsp90 has the structure of formula II. In some embodiments, a labeled compound that binds to Hsp90 has the structure of formula III. In some embodiments, a labeled compound that binds to Hsp90 has the structure of formula IV. In some embodiments, a labeled compound that binds to Hsp90 has the structure of formula V. In some embodiments, a labeled compound that binds to Hsp90 has the structure of formula VI. In some embodiments, a labeled compound that binds to Hsp90 has the structure of formula VII. In some embodiments, a labeled compound that binds to Hsp90 has the structure of formula VIII. In some embodiments, a labeled compound that binds to Hsp90 has the structure of formula IX.

Exemplary assays for measuring binding and/or inhibition of Hsp90 are widely known in the art, for example but not limited to those described in U.S. Pat. No. 7,834,181 and its cited references thereof, the entirety of each of which is hereby incorporated by reference.

Suitable imaging technologies are widely known and practiced in the art. In some embodiments, the imaging process in step (b) of a provided method comprises tomography. In some embodiments, the imaging process comprises positron emission tomography (PET). In some embodiments, the imaging process comprises single-photon emission computed tomography (SPECT). In some embodiments, the imaging process comprises more than one technique. In some embodiments, the imaging process comprises PET combined with another imaging technique. In some embodiments, PET is combined with X-ray Computed Tomography (CT), Magnetic Resonance Imaging (MRI) or single-photon emission computed tomography (SPECT). In some embodiments, the imaging process comprises PET-CT. In some embodiments, the imaging process comprises PET-MRI. In some embodiments, the imaging process comprises PET-SPECT.

In some embodiments, a provided method further comprises collecting electrocardiography (ECG) data. ECG data can be collected prior to, concurrent with, and/or subsequent to the imaging process. In some embodiments, ECG data, among other purposes, are used to solve imaging problems caused by heart motion. ECG-gated imaging is widely known and practiced in the art to improve imaging results including resolution.

In some embodiments, imaging is performed at one time point. In some embodiments, imaging is performed at more than one time point. In some embodiments, imaging is performed at about 0 min, 5 min, 10 min, 15 min, 20 min, 25 min, 30 min, 45 min, 1 hour, 2 hours, 3 hours, 6 hours, 12 hours, 24 hours, 36 hours, 48 hours, 60 hours, 72 hours, 5 days, 6 days, 1 week post-administration of a labeled compound. In some embodiments, imaging is performed at about 0-30 minutes post-administration of a labeled compound. In some embodiments, imaging is performed at about 10-60 minutes post-administration of a labeled compound. In some embodiments, imaging is performed at about 10 min-3 hours post-administration of a labeled compound. In some embodiments, imaging is performed at about 10 min-6 hours post-administration of a labeled compound. In some embodiments, imaging is performed at about 10 min to about 12 hours post-administration of a labeled compound. In some embodiments, imaging is performed at about 10 min to about 24 hours post-administration of a labeled compound. In some embodiments, imaging is performed at about 10 min to about 36 hours post-administration of a labeled compound. In some embodiments, imaging is performed at about 10 min to about 48 hours post-administration of a labeled compound. In some embodiments, imaging is performed at about 10 min to about 72 hours post-administration of a labeled compound. In some embodiments, imaging is performed after about 72 hours post-administration of a labeled compound.

In certain embodiments, imaging of provided methods is performed by detecting a labeled compound in various tissues in a subject that can be affected by an inflammation and/or infection. Any tissue or organ subject to inflammation and/or infection may be so imaged using the methods provided herein. In some embodiments, detecting the labeled compound in the subject comprises measuring signal intensity from the lung of the subject. In some embodiments, detecting the labeled compound in the subject comprises measuring signal intensity from the colon of the subject. In some embodiments, detecting the labeled compound in the subject comprises measuring signal intensity from the skin of the subject. In some embodiments, detecting the labeled compound in the subject comprises measuring signal intensity from the macrophages of the subject. In some embodiments, detecting the labeled compound in the subject comprises measuring signal intensity from the stroma of the subject. In some embodiments, detecting the labeled compound in the subject comprises measuring signal intensity from the cardiac tissue of the subject.

In some embodiments, a provided method further comprises a step of comparing an image from step (b) to a reference. In some embodiments, a reference is the image of healthy tissue within the image. In some embodiments, a reference is an image taken at a different time point for the same subject. In some embodiments, a reference is an average image, wherein the data for each point of the image are the average of the data for that point in two or more images that are averaged. In some embodiments, a reference is an image taken without an inflammation and/or infection present. In some embodiments, a reference is the "average" image of a patient population. In some embodiments, a reference is the average image of a healthy population. In some embodiments, a reference is the average image of a population with an inflammation and/or infection. In some embodiments, an average image is constructed by averaging the signal intensity of each subject in a population for every position of the image. In some embodiments, a reference image is what a trained physician or radiologist knows to be a normal or average image for the tissue being imaged.

In some embodiments, a provided method further comprises a step that includes comparing the data of a first tissue position of an image obtained in step (b) to those of a second tissue position, wherein the second tissue position is from another image or a different tissue position of the same image. In some embodiments, a provided method further comprises a step that includes comparing the data of a first tissue position of an image obtained in step (b) to those of a second tissue position, wherein the second tissue position is from another image. In some embodiments, a provided method further comprises a step that includes comparing the data of a first tissue position of an image obtained in step (b) to those of a second tissue position, wherein the second tissue position is a different position of the same image. In some embodiments, the comparison is a direct comparison. In some embodiments, the comparison is an indirect comparison. In some embodiments, the comparison is an indirect comparison, wherein at least one of the first and second positions is compared to a reference. In some embodiments, a reference is from an average tissue image.

Unless otherwise specified, "imaging" refers to a process of collecting data using a medical imaging device, and an "image" refers to a set of collected data. The set of collected data can be collected, transmitted, stored, processed, analyzed or presented in various formats, including but not limited to visual pictures.

Measuring of signal intensity in images produced from various medical techniques is a standard practice known by a person of ordinary skill in the art. In some embodiments, computer software, sometimes commercially available and/or installed with an imaging instrumentation system, is used to analyze signals collected by an imaging system, including quantitative and qualitative comparison with a reference point and/or a reference image. In some embodiments, a lack of signal, or decreased intensity of signal, when compared to one or more reference points and/or one or more reference images, indicates relatively less inflammation and/or infection in the location that lacks the signal or has decreased intensity of signal. A physician, upon analyzing and interpreting these results, can then make the medically relevant descisions and recommendations on proper treatment.

In some embodiments, Hsp90 is upregulated in areas of inflammations and infections. Therefore, without wishing to be bound by any particular theory, it is believed that an increase in signal could be realized in such instances where a labeled Hsp90 inhibitor is used, particularly one that selectively binds stress-specific Hsp90.

In some embodiments, an inflammation and/or infection is associated with Hsp90. In some embodiments, an inflammation and/or infection is associated with stress-specific Hsp90. In some other embodiments, an inflammation and/or infection is not associated with Hsp90. In some embodiments, a provided tissue imaging method is performed for the diagnosis, treatment, prevention or monitoring of a disease, disorder, or condition on a subject irrespective of the role of Hsp90 in the said disease, disorder, or condition.

In some embodiments, a labeled compound is co-administered with a non-radioactive therapeutic compound. In some embodiments, a labeled compound has the same structure as the non-radioactive therapeutic compound but is labeled by the enrichment of one or more radioactive isotopes of one or more elements. In some embodiments, a labeled compound is administered concurrently with a non-labeled compound. In some embodiments, a labeled compound is administered prior to a non-labeled compound. In some embodiments, a labeled compound is administered subsequent to a non-labeled compound. In some embodiments, concurrent administration uses a formulation comprising a mixture of labeled compound and non-radioactive compound. In some embodiments, a labeled and non-radioactive therapeutic compound are co-administered but via different routes and/or sites of administration. In some embodiments, a non-labeled compound is an Hsp90 inhibitor.

In some embodiments, imaging of a labeled compound, among other things, provides information on the distribution of the co-administered therapeutic compound in tissues affected by an inflammation and/or infection. In some embodiments, imaging measures the accessibility of Hsp90 in the tissue affected by an inflammation and/or infection to a therapeutic compound. In some embodiments, imaging measures the concentrations of a labeled and/or non-labeled therapeutic compound in the tissue affected by an inflammation and/or infection. In some embodiments, imaging measures the concentration of non-labeled therapeutic compound by use of a radiotracer amount of labeled compound. In some embodiments, imaging measures tissue concentrations of radioactivity for labeled-compound administered at a therapeutically effective amount. In some embodiments, imaging measures the occupancy or saturation of Hsp90 achieved by a therapeutic compound in the tissue affected by an inflammation and/or infection. In some embodiments, imaging measures the ability of a therapeutic compound to displace the labeled compound in the tissue affected by an inflammation and/or infection.

The radioactive isotopes of radiolabeled compounds decay with time. As known by a person having ordinary skill in the art, for different purposes radiolabeled compounds with different half-life can be used. In some embodiments, a radioactive label or a radiolabeled compound has a half-life of at least about 0.1, 0.2, 0.5, 1, 2, 3, 4, 5, 6, 7, 8, 9, 10, 11, 12, 18, 24, 36, 48, 72, 96, or 100.3 hours. In some embodiments, a radioactive label or a radiolabeled compound has a half-life of at least about 1 hour. In some embodiments, a radioactive label or a radiolabeled compound has a half-life of at least about 2 hours. In some embodiments, a radioactive label or a radiolabeled compound has a half-life of at least about 3 hours. In some embodiments, a radioactive label or a radiolabeled compound has a half-life of at least about 4 hours. In some embodiments, a radioactive label or a radiolabeled compound has a half-life of at least about 5 hours. In some embodiments, a radioactive label or a radiolabeled compound has a half-life of at least about 6 hours. In some embodiments, a radioactive label or a radiolabeled compound has a half-life of at least about 7 hours. In some embodiments, a radioactive label or a radiolabeled compound has a half-life of at least about 8 hours. In some embodiments, a radioactive label or a radiolabeled compound has a half-life of at least about 9 hours. In some embodiments, a radioactive label or a radiolabeled compound has a half-life of at least about 10 hours. In some embodiments, a radioactive label or a radiolabeled compound has a half-life of at least about 11 hours. In some embodiments, a radioactive label or a radiolabeled compound has a half-life of at least about 12 hours. In some embodiments, a radioactive label or a radiolabeled compound has a half-life of at least about 18 hours. In some embodiments, a radioactive label or a radiolabeled compound has a half-life of at least about 24 hours. In some embodiments, a radioactive label or a radiolabeled compound has a half-life of at least about 36 hours. In some embodiments, a radioactive label or a radiolabeled compound has a half-life of at least about 48 hours. In some embodiments, a radioactive label or a radiolabeled compound has a half-life of at least about 72 hours. In some embodiments, a radioactive label or a radiolabeled compound has a half-life of at least about 96 hours. In some embodiments, a radioactive label or a radiolabeled compound has a half-life of about 59.4 days. In some embodiments, a radioactive label or a radiolabeled compound has a half-life of about 8.0 days. In some embodiments, a radioactive label or a radiolabeled compound has a half-life of about 60 days. In some embodiments, a radiolabelled compound comprises radioactive labels having different half-lives.

It will be appreciated that the comparison of images taken at different time points, including but not limited to before and after an inflammation and/or infection, are useful in the diagnosis or treatment of the inflammation and/or infection. In some embodiments, an image before an inflammation and/or infection is used as a reference image, to which another image is compared. In some embodiments, a second image of a tissue affected by an inflammation and/or infection is collected after a first image of the tissue is collected. In some embodiments, a provided method comprises a step of comparing a second image to a first image. In some embodiments, a provided method comprises a step of comparing a second image to a first image, comprising normalizing the signal intensity of each region of the second image to the first image. In some embodiments, a provided method comprises a step of comparing a second image to a first image, comprising normalizing the signal intensity of each region of the second image relative to the first image, wherein weaker normalized signal intensity indicates presence of less Hsp90. In some embodiments, weaker normalized signal indicates presence of less stress-specific Hsp90. In some embodiments, weaker normalized signal indicates improvement of an inflammation and/or infection. In some embodiments, weaker normalized signal indicates that an existing treatment ameliorates an inflammation and/or infection.

In some embodiments, the present invention provides a method for the diagnosis of an inflammation and/or infection in a tissue, comprising administering a labeled compound of any of formula I to IX to a subject in need thereof, and imaging the tissue by detecting the labeled compound in the subject. In some embodiments, the disease or condition is psoriasis. In some embodiments, an inflammation and/or infection is associated with abnormal Hsp90 expression or protein levels in a tissue. In some embodiments, an inflammation and/or infection is abnormal Hsp90 expression or protein levels in an tissue. In some embodiments, abnormal Hsp90 expression or protein levels in a tissue affected by an inflammation and/or infection are higher than the expression or levels in a normal healthy tissue. In some embodiments, abnormal Hsp90 expression or protein level in a tissue affected by an inflammation and/or infection is lower than the expression or levels in a normal healthy tissue. In some embodiments, an abnormal Hsp90 expression or protein level in a tissue affected by an inflammation and/or infection comprises Hsp90 isoforms in ratios different than a normal healthy tissue.

In some embodiments, the present invention provides a method for the treatment of a tissue affected by, or prevention of an tissue from, an inflammation and/or infection, comprising administering a labeled compound of any of formula I to IX to a subject in need thereof, and imaging the tissue by detecting the labeled compound in the subject.

In some embodiments, the present invention provides a method for monitoring the effect of an inflammation and/or infection treatment in a subject in need thereof, comprising steps of:
 (a) administering a labeled compound of any of formula I to IX to the subject who is scheduled for the inflammation and/or infection treatment, currently undergoing the inflammation and/or infection treatment, or has completed or discontinued the inflammation and/or infection treatment;
 (b) imaging a tissue affected by the inflammation and/or infection by detecting the labeled compound; and
(c) recommending to the subject an appropriate avoidance, continuation, modification, or termination in the inflammation and/or infection treatment.

In some embodiments, a treatment described herein includes, but is not limited to, use of an anti-inflammatory drug or anti-infective drug, as described herein.

In some embodiments, the present invention provides a method for monitoring an inflammation and/or infection treatment regimen, comprising steps of:
(a) administering a labeled compound of any of formula I to IX to a subject under the inflammation and/or infection treatment regimen;

(b) imaging a tissue affected by the inflammation and/or infection by detecting the labeled compound in the subject;
(c) analyzing the images from step (b); and
(d) maintaining, modifying, or discontinuing the inflammation and/or infection treatment regimen.

Patient stratification is important for clinical trials, preventative medicine, and treatment. In some embodiments, the present invention provides methods for patient stratification based on inflammation and/or infection imaging. In some embodiments, the present invention provides a method for selecting subjects for an inflammation and/or infection treatment, comprising steps of:
(a) administering a labeled compound of any of formula I to IX to a subject;
(b) imaging a tissue affected by the inflammation and/or infection by detecting the labeled compound in the subject;
(c) analyzing the images from step (b); and
(d) including or excluding the subject for the treatment.

In some embodiments, the presence of a labeled compound in a tissue indicates the presence of inflammation and/or infection, and to include the subject for the treatment. In some embodiments, abnormal signal compared to a reference, as provided herein, indicates affection by an inflammation and/or infection, and to include the subject for the treatment. The abnormal signal can be increased or decreased compared to a reference, as provided herein. In some embodiments, the absence of a labeled compound in a tissue indicates no inflammation and/or infection is present, and to exclude the subject for the treatment.

In some embodiments, a treatment comprises the use of a compound that binds to Hsp90. In some embodiments, a treatment comprises the use of an Hsp90 inhibitor, also referred to as a "Hsp90 inhibition therapy" or "Hsp90 therapy". In some embodiments, the method for selecting a subject is for a clinical trial. In some embodiments, the method for selecting a subject is for a clinical trial of a new therapy or diagnosis. In some embodiments, the method for selecting a subject is for a clinical trial of a new therapy or diagnosis for an inflammation and/or infection.

In some embodiments, a provided method provides an approach to patient screening, distinguishing patients likely to have either a favorable or unfavorable therapeutic response to a compound that binds to Hsp90 for an inflammation and/or infection treatment. In some embodiments, a provided method provides an approach to patient screening, distinguishing patients likely to have either a favorable or unfavorable therapeutic response to a compound for an inflammation and/or infection treatment, wherein the compound is an unlabeled counterpart of a compound of any of formula I to IX.

In some embodiments, the present invention provides a method for the treatment of a tissue affected by, or prevention of a tissue from, an inflammation and/or infection, comprising the step of administering a compound of any of formula I to IX to a subject in need thereof.

In some embodiments, the present invention provides a method for selecting subjects for an inflammation and/or infection treatment, comprising steps of:
(a) administering to a subject a labeled compound that binds to stress-specific Hsp90; and
(b) imaging a tissue affected by the inflammation and/or infection by detecting the labeled compound in the subject;
wherein increased uptake of the labeled compound indicates more likelihood for the subject to benefit from the treatment.

In some embodiments, an inflammation and/or infection treatment comprises the use of a compound that binds to Hsp90. In some embodiments, an inflammation and/or infection treatment comprises the use of a compound that binds to stress-specific Hsp90. In some embodiments, an inflammation and/or infection treatment comprises the use of the non-labeled counterpart of a labeled compound described herein.

Dosing is often a key aspect of a treatment regimen. In some embodiments, the present invention provides a method for optimizing the dosage of a drug based on imaging, so that the desired therapeutic effects can be achieved with minimal side effects. In some embodiments, the present invention provides a method for determining the dosage of a drug for the treatment of an inflammation and/or infection, comprising steps of:
(a) administering a labeled compound of any of formula I to IX to a subject;
(b) imaging a tissue affected by the inflammation and/or infection by detecting the labeled compound in the subject;
(c) analyzing the images from step (b); and
(d) administering to the subject a suitable amount of the drug.

In some embodiments, a provided method comprises determining the effective dosage of a drug. In some embodiments, a provided method comprises determining the toxicity of a drug in the subject. In some embodiments, a provided method comprises determining the minimum effective dosage of a drug. In some embodiments, a provided method comprises determining the highest toxicity dosage for a subject. In some embodiments, a provided method comprises determining the highest tolerable dosage for a subject. In some embodiments, a provided method comprises determining the balance between efficacy and toxicity and/or safety.

In some embodiments, a provided method further comprises administering a non-radioactive therapeutic amount of a compound that binds to Hsp90. In some embodiments, analyzing the images in provided methods is done with comparison to images obtained when administering only the labeled compound. In some embodiments, the labeled compound is administered before, during, or after administration of a non-radioactive therapeutic compound.

In some embodiments, the imaging of a provided method is non-invasive.

In some embodiments, a provided method comprises identifying abnormal signal compared to a reference, wherein the abnormal signal indicates an inflammation and/or infection in the tissue. In some embodiments, an increased signal (e.g., a "hot spot") indicates an inflammation and/or infection in the tissue. In some embodiments, a descreased signal (e.g., a "cold spot") indicates inflammation and/or infection in the tissue. It will be appreciated that in such instances, "hot" or "cold" is relative to the amount of labeled compound that normally accumulates in surrounding healthy tissue. Without wishing to be bound by any theory, local destruction of living tissue by an inflammation and/or infection may cause less Hsp 90 targeted binding, resulting in decreased signals as compared to the reference, e.g., surrounding healthy tissues in the organ. As such, in certain embodiments, a decreased signal or "cold spot" indicates an inflammation and/or infection in the tissue. The skilled artisan will be familiar with the relevant context and be able to ascertain whether an increased or decreased signal (i.e., contrast in signal relative to surrounding or normal tissue) is indicative of an inflammation or infection. Also without wishing to be bound by any theory, in some embodiments, tissues (e.g., the liver) are known to accumulate metabolites of Hsp90 inhibitors, and may therefore manifest as locales of apparent high uptake when in fact the signal is not representative of compound bound to Hsp90. Such embodiments are known to the skilled artisan and are to be taken into account when assessing the relative signal of "hot" or "cold" spots near or within such tissues.

In some embodiments, a provided method comprises identifying decreased signal compared to a reference, wherein the decreased signal indicates amelioration of an inflammation and/or infection in the tissue. In some embodiments, the decreased signal is preceded by a period of increased signal compared to a reference, for example a "flare response" where labeled compound uptake in a tissue increases after treatment, then later subsides. The period of increased signal can be 0.5 hr, 1 hr, 2 hrs, 3 hrs, 4 hrs, 5 hrs, 6 hrs, 7 hrs, 8 hrs, 9 hrs, 10 hrs, 12 hrs, 15 hrs, 18 hrs, 21 hrs, or 24 hrs or more after commencing treatment.

In some embodiments, a subject in a provided method is a cancer patient.

Exemplary Drugs, Including Non-Hsp90 Targeting Drugs

In some embodiments, a drug used in provided methods is an anti-inflammatory drug. Exemplary anti-inflammatory drugs are well known and prescribed in the art. In some embodiments, drugs can be active agents used conventionally for immunosuppression or for inflammatory conditions, allergic disorders, or immune disorders, which include, but are not limited to, steroids, non-steroidal anti-inflammatory agents, antihistamines, analgesics, immunosuppressive agents, and suitable mixtures thereof.

Exemplary non-steroidal anti-inflammatory agents include, but are not limited to, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone and pharmaceutically acceptable salts thereof and mixtures thereof. For additional description of the NSAIDs, see Paul A. Insel, Analgesic-Antipyretic and Anti-inflammatory Agents and Drugs Employed in the Treatment of Gout, in Goodman & Gilman's The Pharmacological Basis of Therapeutics 617-57 (Perry B. Molinhoff and Raymond W. Ruddon eds., 9.sup.th ed 1996) and Glen R. Hanson, Analgesic, Antipyretic and Anti-Inflammatory Drugs in Remington: The Science and Practice of Pharmacy Vol II 1196-1221 (A. R. Gennaro ed. 19th ed. 1995) which are hereby incorporated by reference in their entireties.

Exemplary antihistamines include, but are not limited to, loratadine, cetirizine, fexofenadine, desloratadine, diphenhydramine, chlorpheniramine, chlorcyclizine, pyrilamine, promethazine, terfenadine, doxepin, carbinoxamine, clemastine, tripelennamine, brompheniramine, hydroxyzine, cyclizine, meclizine, cyproheptadine, phenindamine, acrivastine, azelastine, levocabastine, and mixtures thereof. For additional description of antihistamines, see Goodman & Gilman's The Pharmacological Basis of Therapeutics (2001) 651-57, 10.sup.th ed).

Exemplary immunosuppressive agents include, but are not limited to, glucocorticoids, corticosteroids (such as Prednisone or Solumedrol), T cell blockers (such as cyclosporin A and FK506), purine analogs (such as azathioprine (Imuran)), pyrimidine analogs (such as cytosine arabinoside), alkylating agents (such as nitrogen mustard, phenylalanine mustard, busifan, and cyclophosphamide), folic acid antagonists (such as aminopterin and methotrexate), macrolides (such as rapamycin), antibiotics (such as actinomycin D, mitomycin C, puramycin, and chloramphenicol), human IgG, antilymphocyte globulin (ALG), and antibodies (such as anti-CD3 (OKT3), anti-CD4 (OKT4), anti-CD5, anti-CD7, anti-IL-2 receptor, anti-alpha/beta TCR, anti-ICAM-1, anti-CD20 (Rituxan), anti-IL-12 and antibodies to immunotoxins).

In some embodiments, a drug is an anti-infective drug. Exemplary anti-infective drugs are well known and prescribed in the art.

In some embodiments, a drug is an anti-viral agent. Nonlimiting examples of anti-viral agents are protease inhibitors (e.g., nafamostat, camostat, gabexate, epsilonaminocapronic acid and aprotinin), fusion inhibitors (e.g., BMY-27709, CL 61917, and CL 62554), M2 proton channel blockers (e.g., Amantadine and Rimantadine), polymerase inhibitors (e.g., 2-deoxy-2'fluoroguanosides (2'-fluoroGuo), 6-fluoro-3-hydroxy-2-pyrazinecarboxamide (T-705), T-705-4-ribofuranosyl-5'-triphosphate (T-705RTP)), endonuclease inhibitors (e.g., L-735,822 and flutimide), kinase inhibitors (e.g., U0126 (a MEK inhibitor), PD098059 (a MEK-specific inhibitor), PD-184352/CI-1040 (a MEK inhibitor), PD 0325901 (a MEK inhibitor), ARRY-142886/AZD-6244 (a MEK1 and MEK2 inhibitor)), neuraminidase inhibitors (e.g., Zanamivir (Relenza), Oseltamivir (Tamiflu), Peramivir and ABT-675 (A-315675)), all of which are described in Hsieh et al., Current Pharmaceutical Design, 2007, 13, 3531-3542. Other examples of antiviral drugs include, but are not limited to, reverse transcriptase inhibitor (e.g., Abacavir, Adefovir, Delavirdine, Didanosine, Efavirenz, Emtricitabine, Lamivudine, Nevirapine, Stavudine, Tenofovir, Tenofovir disoproxil, and Zalcitabine) Aciclovir, Acyclovir, protease inhibitor (e.g., Amprenavir, Indinavir, Nelfinavir, Ritonavir, and Saquinavir), Arbidol, Atazanavir, Atripla, Boceprevir, Cidofovir, Combivir, Darunavir, Docosanol, Edoxudine, entry inhibitors (e.g., Enfuvirtide and Maraviroc), Entecavir, Famciclovir, Fomivirsen, Fosamprenavir, Foscamet, Fosfonet, Ganciclovir, Ibacitabine, Immunovir, Idoxuridine, Imiquimod, Inosine, integrase inhibitor (e.g., Raltegravir), interferons (e.g., types I, II, and III), Lopinavir, Loviride, Moroxydine, Nexavir, nucleoside analogues (e.g., Aciclovir), Penciclovir, Pleconaril, Podophyllotoxin, Ribavirin, Tipranavir, Trifluridine, Trizivir, Tromantadine, Truvada, Valaciclovir (Valtrex), Valganciclovir, Vicriviroc, Vidarabine, Viramidine, and Zidovudine.

In some embodiments, a drug is an anti-fungal agent. Nonlimiting anti-fungal agents are imidazoles, FK 463, amphotericin B. BAY 38-9502, MK 991, pradimicin, UK 292, butenafine, chitinase, 501 cream, Acrisorcin; Ambruticin; Amorolfine, Amphotericin B; Azaconazole; Azaserine; Basifungin; Bifonazole; Biphenamine Hydrochloride; Bispyrithione Magsulfex; Butoconazole Nitrate; Calcium Undecylenate; Candicidin; Carbol-Fuchsin; Chlordantoin;

Ciclopirox; Ciclopirox Olamine; Cilofungin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Isoconazole; Itraconazole; Kalafungin; Ketoconazole; Lomofungin; Lydimycin; Mepartricin; Miconazole; Miconazole Nitrate; Monensin; Monensin Sodium; Naftifine Hydrochloride; Neomycin Undecylenate; Nifuratel; Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Proclonol; Pyrithione Zinc; Pyrrolnitrin; Rutamycin; Sanguinarium Chloride; Saperconazole; Scopafungin; Selenium Sulfide; Sinefungin; Sulconazole Nitrate; Terbinafine; Terconazole; Thiram; Ticlatone; Tioconazole; Tolciclate; Tolindate; Tolnaftate; Triacetin; Triafungin; Undecylenic Acid; Viridofulvin; Zinc Undecylenate; and Zinoconazole Hydrochloride.

In some embodiments, a drug is an antibacterial agent. In some embodiments, antibacterial agents are antibiotics of the beta-lactam group such as natural penicillins, semisynthetic penicillins, natural cephalosporins, semisynthetic cephalosporins, cephamycins, 1-oxacephems, clavulanic acids, penems, carbapenems, nocardicins, monobactams; tetracyclines, anhydrotetracyclines, anthracyclines; aminoglycosides; nucleosides such as N-nucleosides, C-nucleosides, carbocyclic nucleosides, blasticidin S; macrolides such as 12-membered ring macrolides, 14-membered ring macrolides, 16-membered ring macrolides; ansamycins; peptides such as bleomycins, gramicidins, polymyxins, bacitracins, large ring peptide antibiotics containing lactone linkages, actinomycins, amphomycin, capreomycin, distamycin, enduracidins, mikamycin, neocarzinostatin, stendomycin, viomycin, virginiamycin; cycloheximide; cycloserine; variotin; sarkomycin A; novobiocin; griseofulvin; chloramphenicol; mitomycins; fumagillin; monensins; pyrrolnitrin; fosfomycin; fusidic acid; D-(p-hydroxyphenyl) glycine; D-phenylglycine; or enediynes.

In some embodiments, a drug is an antibiotic selected from benzylpenicillin (potassium, procaine, benzathine), phenoxymethylpenicillin (potassium), phenethicillin potassium, propicillin, carbenicillin (disodium, phenyl sodium, indanyl sodium), sulbenicillin, ticarcillin disodium, methicillin sodium, oxacillin sodium, cloxacillin sodium, dicloxacillin, flucloxacillin, ampicillin, mezlocillin, piperacillin sodium, amoxicillin, ciclacillin, hectacillin, sulbactam sodium, talampicillin hydrochloride, bacampicillin hydrochloride, pivmecillinam, cephalexin, cefaclor, cephaloglycin, cefadroxil, cephradine, cefroxadine, cephapirin sodium, cephalothin sodium, cephacetrile sodium, cefsulodin sodium, cephaloridine, cefatrizine, cefoperazone sodium, cefamandole, vefotiam hydrochloride, cefazolin sodium, ceftizoxime sodium, cefotaxime sodium, cefmenoxime hydrochloride, cefuroxime, ceftriaxone sodium, ceftazidime, cefoxitin, cefmetazole, cefotetan, latamoxef, clavulanic acid, imipenem, aztreonam, tetracycline, chlortetracycline hydrochloride, demethylchlortetracycline, oxytetracycline, methacycline, doxycycline, rolitetracycline, minocycline, daunorubicin hydrochloride, doxorubicin, aclarubicin, kanamycin sulfate, bekanamycin, tobramycin, gentamycin sulfate, dibekacin, amikacin, micronomicin, ribostamycin, neomycin sulfate, paromomycin sulfate, streptomycin sulfate, dihydrostreptomycin, destomycin A, hygromycin B, apramycin, sisomicin, netilmicin sulfate, spectinomycin hydrochloride, astromicin sulfate, validamycin, kasugamycin, polyoxin, blasticidin S, erythromycin, erythromycin estolate, oleandomycin phosphate, tracetyloleandomycin, kitasamycin, josamycin, spiramycin, tylosin, ivermectin, midecamycin, bleomycin sulfate, peplomycin sulfate, gramicidin S, polymyxin B, bacitracin, colistin sulfate, colistinmethanesulfonate sodium, enramycin, mikamycin, virginiamycin, capreomycin sulfate, viomycin, enviomycin, vancomycin, actinomycin D, neocarzinostatin, bestatin, pepstatin, monensin, lasalocid, salinomycin, amphotericin B, nystatin, natamycin, trichomycin, mithramycin, lincomycin, clindamycin, clindamycin palmitate hydrochloride, flavophospholipol, cycloserine, pecilocin, griseofulvin, chloramphenicol, chloramphenicol palmitate, mitomycin C, pyrrolnitrin, fosfomycin, fusidic acid, bicozamycin, tiamulin, or siccanin.

In some embodiments, a drug is an anti-parasitic agent. Nonlimiting examples of anti-parasitic agents are albendazole, amphotericin B, benznidazole, bithionol, chloroquine HCl, chloroquine phosphate, clindamycin, dehydroemetine, diethylcarbamazine, diloxanide furoate, eflomithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethroprim-sulfamethoxazole, and tryparsamide.

In some embodiments, a drug is a compound having the structure of formula X wherein each variable is independently as described in classes and subclasses herein, both singly and in combination.

Non-Radioactive Therapeutic Compounds

In some embodiments, provided methods use a non-radioactive therapeutic compound alone or in combination with the exemplary drugs named above.

In some embodiments, the non-radioactive therapeutic compound used in a provided method binds to Hsp90. In some embodiments, the non-radioactive therapeutic compound is an Hsp90 inhibitor. In some embodiments, the non-radioactive compound is a natural product or its derivatives. In some embodiments, the non-radioactive compound is Geldanamycin or its derivative. In some embodiments, the non-radioactive compound is radicicol or its derivative. In some embodiments, the non-radioactive compound is Gamitrinib or its derivative.

In some embodiments, the non-radioactive compound has the structure of formula X:

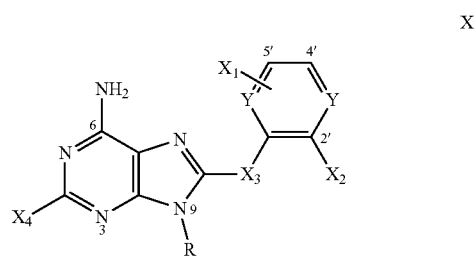

or its pharmaceutically acceptable salt thereof, wherein:
each Y is independently CH or N;
R is hydrogen, a $C_1$ to $C_{10}$ alkyl, alkenyl, alkynyl, or an alkoxyalkyl group, optionally comprising one or more heteroatoms, or a targeting moiety connected to N9 via a linker;
$X_4$ is hydrogen or halogen;
$X_3$ is $CH_2$, $CF_2$, S, SO, $SO_2$, O, NH, or $NR^2$, wherein $R^2$ is alkyl;
$X_2$ is halogen, alkyl, alkoxy, halogenated alkoxy, hydroxyalkyl, pyrollyl, optionally substituted aryloxy, alkylamino, dialkylamino, carbamyl, amido, alkylamido, dialkylamido, acylamino, alkylsulfonylamido, trihalomethoxy, trihalocarbon, thioalkyl, C(O)O-alkyl, $NH_2$, OH, CN, $SO_2X_5$, $NO_2$, NO, C(S)R, $NHSO_2X_5$, or C(O)R, where $X_5$ is F, $NH_2$, alkyl, or H, and $R_2$ is alkyl, $NH_2$, NH-alkyl, or O-alkyl; and
$X_1$ represents two substituents, which may be the same or different, disposed in the 4' and 5' positions on the aryl group, wherein $X_1$ is selected from halogen, alkyl, alkoxy, halogenated alkoxy, hydroxyalkyl, pyrollyl, optionally substituted aryloxy, alkylamino, dialkylamino, carbamyl, amido, alkylamido, dialkylamido, acylamino, alkylsulfonylamido, trihalomethoxy, trihalocarbon, thioalkyl, COO-alkyl, $NH_2OH$, CN, $SO_2X_5$, $NO_2$, NO, C(S)R, $NHSO_2X_5$, or C(O)R, where $X_5$ is F, $NH_2$, alkyl, or H, and $R_2$ is alkyl, $NH_2$, NH-alkyl, or O-alkyl, $C_1$ to $C_6$ alkyl or alkoxy, or wherein $X_1$ has the formula —O—$(CH_2)_n$—O—, wherein n is an integer from 1 to 2, and one of the oxygens is bonded at the 5'-position and the other at the 4'-position of the aryl ring.

In some embodiments, the non-radioactive compound is a non-radioactive counterpart of a compound having the structure of any of formula III to IX.

In some embodiments, the non-radioactive therapeutic compound is compound A:

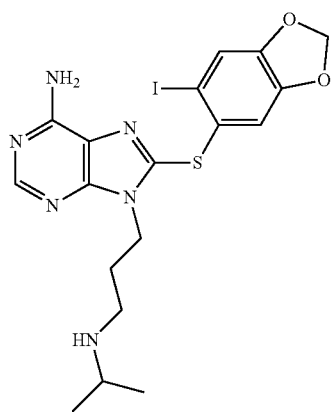 [SMILES: CC(C)NCCCn1c(Sc2cc3c(cc2I)OCO3)nc2c(N)ncnc21]

Labeled Compounds

In some embodiments, a labeled compound is a labeled compound of formula I, wherein the prior-labeling compound has the structure of formula I. In some embodiments, a labeled compound that binds to Hsp90 is a labeled compound of formula I. In some embodiments, the labeled compound that binds to Hsp90 has the structure of any one of formula II to IX. In some embodiments, the labeled compound that binds to Hsp90 is a labeled natural product or its derivative. In some embodiments, the labeled compound is labeled Geldanamycin or its derivative. In some embodiments, the labeled compound is labeled radicicol or its derivative. In some embodiments, the labeled compound is labeled Gamitrinib or its derivative. Exemplary non-labeled compounds that bind to Hsp90 and may be labeled are widely known in the art, including but not limited to those described in Jhaveri and Modi, HSP90 inhibitors for cancer therapy and overcoming drug resistance, *Adv Pharmacol.* 2012; 65:471-517; and Taldone et al, Design, synthesis, and evaluation of small molecule Hsp90 probes, *Bioorg Med Chem.* 2011; 19(8):2603-14; U.S. Pat. Nos. 8,178,687 and 8,324,240; United States Patent Application Publication Nos. US2012/0277257, US2012/0264770, US2012/0237508, US2013/0045983, US2005/0107343, US2008/0234314, and US2012/0046266; and PCT patent application publication WO2008/115719, WO2008/118391, WO2004/097428, WO2006/098761, WO2006/123165, WO2007/134677, WO2008/093075, WO2007/104944, WO2009/097578, WO2008/118391, WO2007/134298 and WO2006/117669; the entirety of each of which is hereby incorporated by reference. All these compounds, among others, can be labeled using known chemistry in the art and be used in the provided methods described herewith.

In some embodiments, a labeled compound of formula I has the structure of formula II,

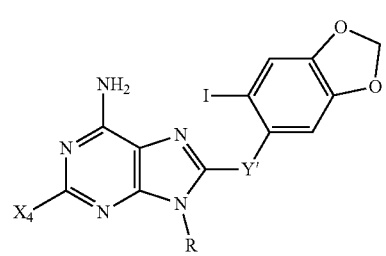

wherein Y' is —$CH_2$— or S;

$X_4$ is hydrogen or halogen; and R is an amino alkyl moiety, optionally substituted on the amino nitrogen with one or two carbon-containing substituents selected independently from the group consisting of alkyl, alkenyl and alkynyl substituents, wherein the total number of carbons in the amino alkyl moiety is from 1 to 9.

In some embodiments, the labeled compound of formula I is an labeled analog of compound A (PUH71):

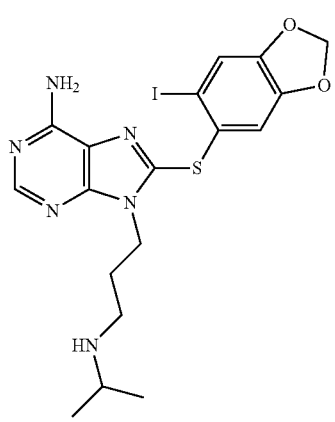 [SMILES: CC(C)NCCCn1c(Sc2cc3c(cc2I)OCO3)nc2c(N)ncnc21]

wherein the labeled compound has at least one atom or substituent detectable by a medical imaging technique.

In some embodiments, a labeled compound A is labeled at 2'-iodo. In some embodiments, a labeled compound A has $^{123}$I at the 2'-iodo position. In some embodiments, a labeled compound A has $^{123}$I at the 2'-iodo position and is used for SPECT imaging. In some embodiments, a labeled compound A has $^{124}$I at the 2'-iodo position. In some embodiments, a labeled compound A has $^{124}$I at the 2'-iodo position and is used for PET imaging.

In some embodiments, a labeled compound of any of formula I to IX is labeled through substituting a hydrogen atom with a group that can be detected by a medical imaging technique. In some embodiments, a labeled compound of any of formula I to IX is labeled through substituting at least one hydrogen atom in the compound with at least one group that produces higher signal intensity than the at least one hydrogen atom. In some embodiments, a labeled compound of any of formula I to IX is radiolabeled. In some embodiments, a labeled compound comprises an isotope which decays by positron emission. In some embodiments, a labeled compound is labeled with one or more isotopes selected from $^{124}$I, $^{11}$C, $^{15}$O, $^{13}$N, and $^{18}$F. In some embodiments, a labeled compound is labeled with $^{124}$I. In some embodiments, a compound labeled with $^{124}$I is used in PET imaging. In some embodiments, a compound labeled with $^{123}$I is used in SPECT imaging. In some embodiments, a labeled compound comprises an isotope that decays by electron capture. In some embodiments, a labeled compound comprises an isotope selected from $^{123}$I and $^{131}$I. In some embodiments, a labeled compound comprises one or more labels suited for magnetic resonance imaging (MRI). In some embodiments, a labeled compound comprises one or more $^{19}$F. In some embodiments, a compound labeled with one or more $^{19}$F is used for MRI.

In some embodiments, a label is a fluorophore moiety. In some embodiments, a label is a nanometer-sized agent. In some embodiments, a label is a nanoparticle. In some embodiments, a label is a nanotube. In some embodiments, a label is liposome. In some embodiments, a nanotube or liposome comprises a moiety that produces an enhanced signal. In some embodiments, one or more MRI agents are linked or packaged in a nanotube, nanoparticle or liposome. In some embodiments, one nanometer-sized agent or nanoparticle or liposomal micelle is used to label more than one molecule a compound to be labeled; for example, more than one molecule of the compound to be labeled can be linked to a single nanoparticle. In some embodiments, a label is covalently linked to a compound. In some embodiments, a label is non-covalently linked to a compound.

In some embodiments, a labeled compound is selected from

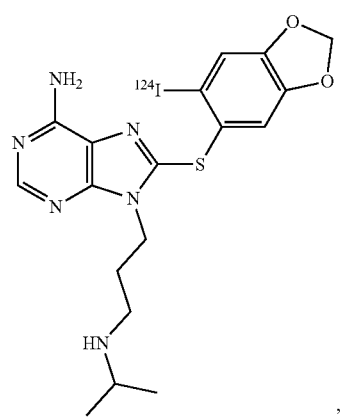

,

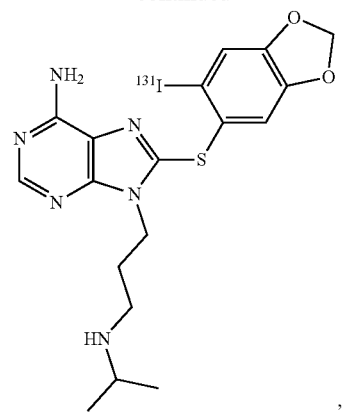

,

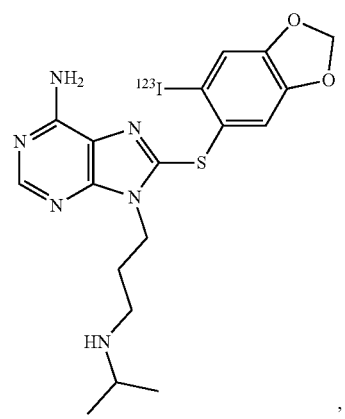

,

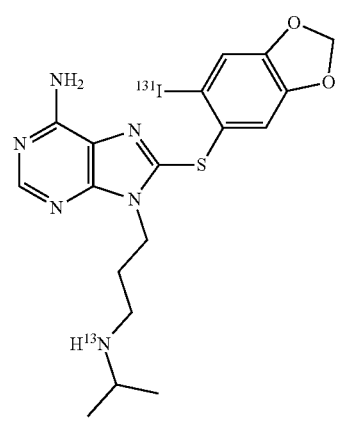 [SMILES: CC(C)NCCCn1c(Sc2cc3c(cc2I)OCO3)nc2c(N)ncnc21]

,

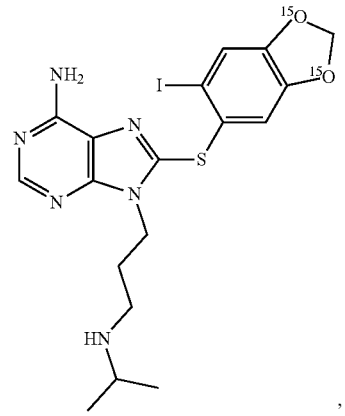

,

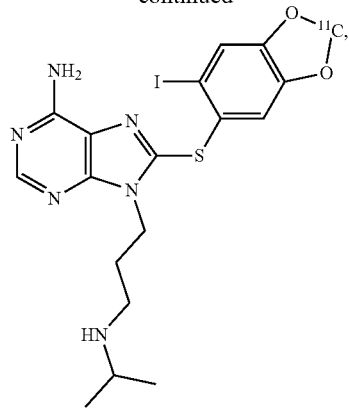
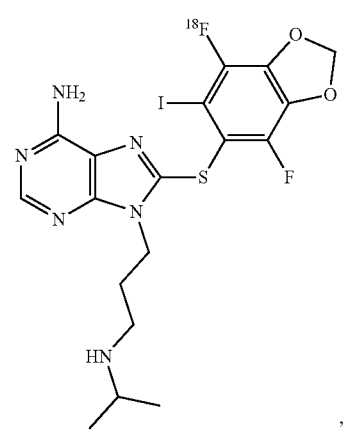
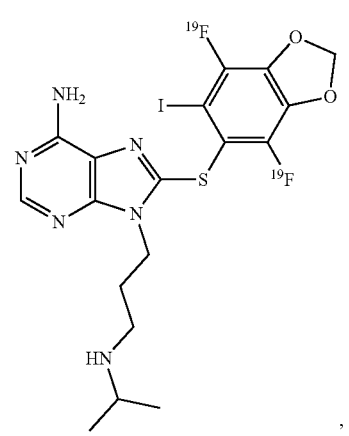

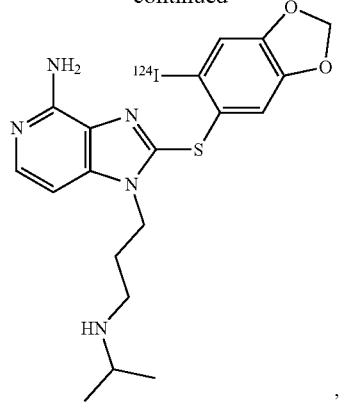
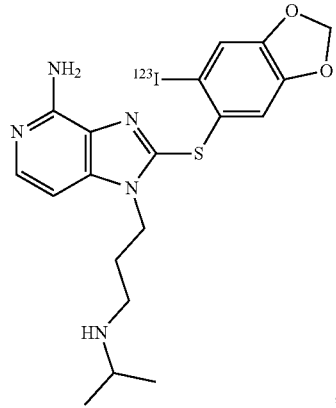
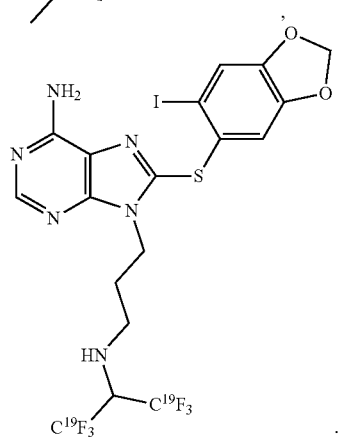

In some embodiments, a compound is labeled without changing the affinity, selectivity or biodistribution profile of the inhibitor. Such labeled compounds are useful as probes for prognostic and/or diagnostic purposes. In one embodiment, a labeled compound is an iodine 124 radiolabeled version of an HSP90 inhibitor or a compound having the structure of any of formula I to IX. In one embodiment, a labeled compound is an iodine 123 radiolabeled version of an HSP90 inhibitor or a compound having the structure of any one of formula I to IX. In one embodiment, a labeled compound is an iodine 131 radiolabeled version of an HSP90 inhibitor or a compound having the structure of any one of formula I to IX. In one embodiment, a labeled compound is an iodine 125 radiolabeled version of an HSP90 inhibitor or a compound having the structure of any one of formula I to IX.

In another embodiment, a radiolabeled compound in a provided method is selected from a compound having the following formulae:

43
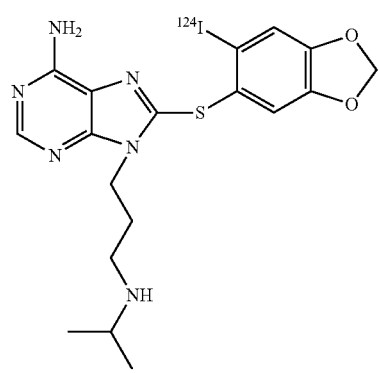
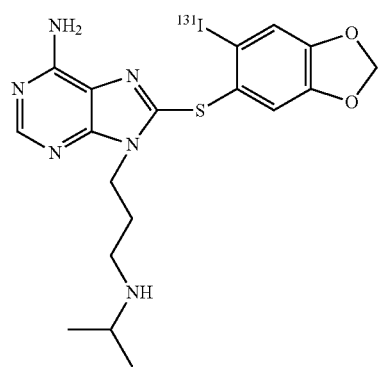
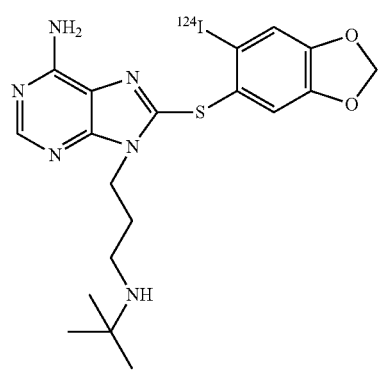
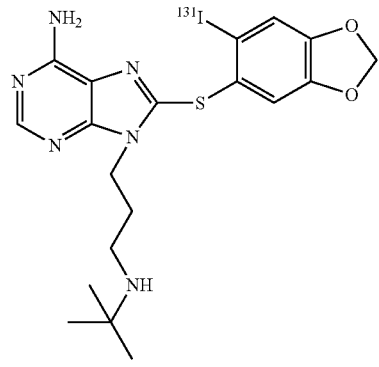
44
-continued
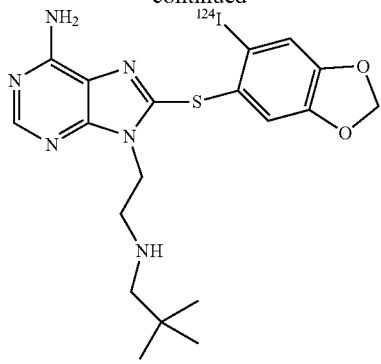
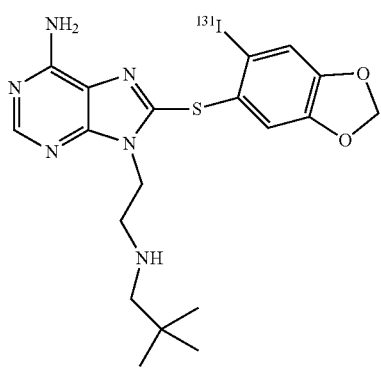
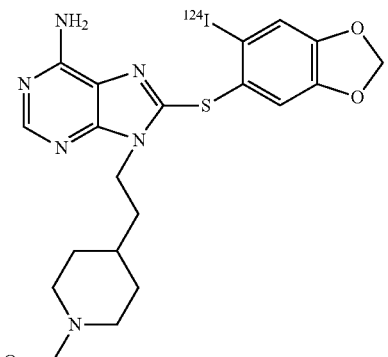
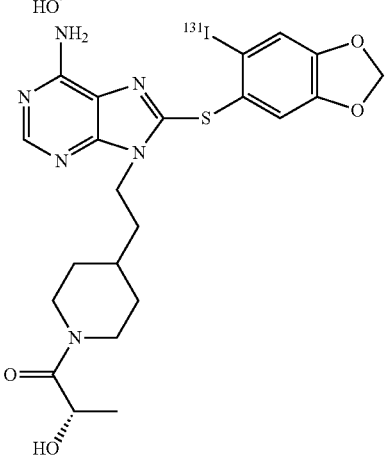

45
-continued
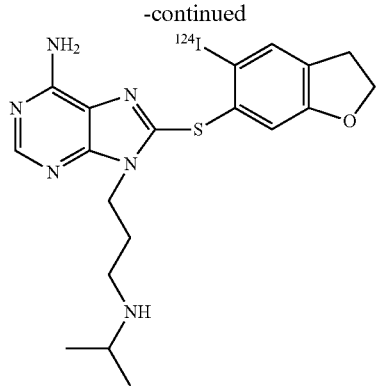
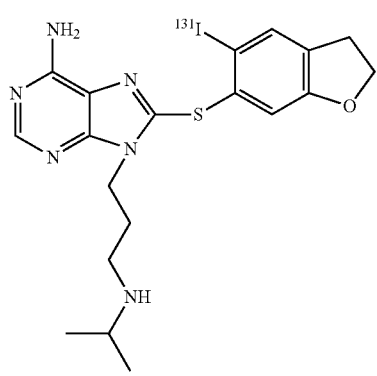
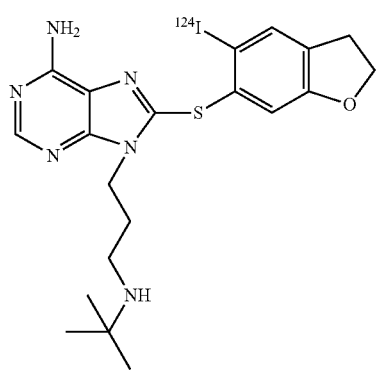
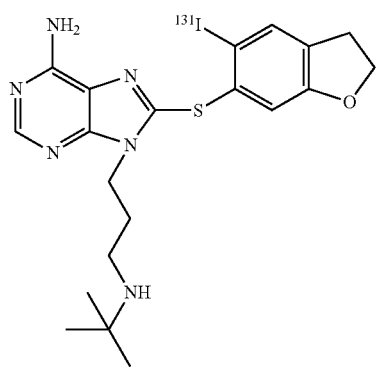
46
-continued
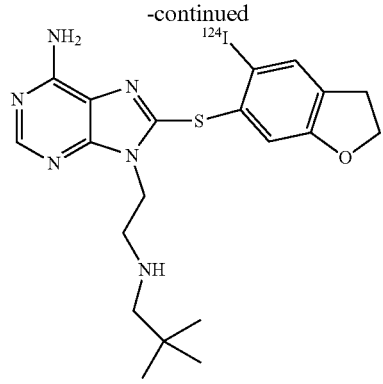
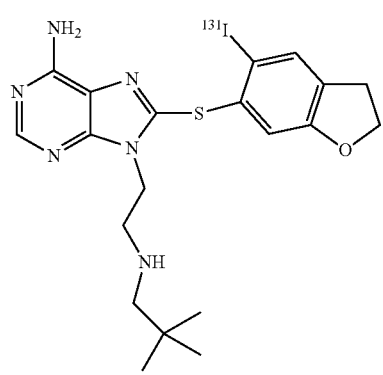
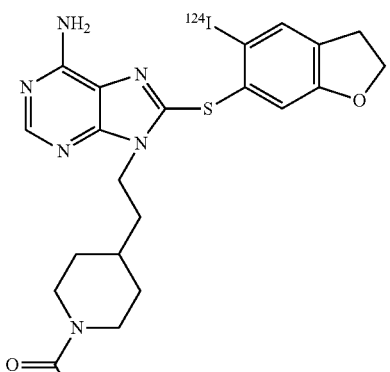
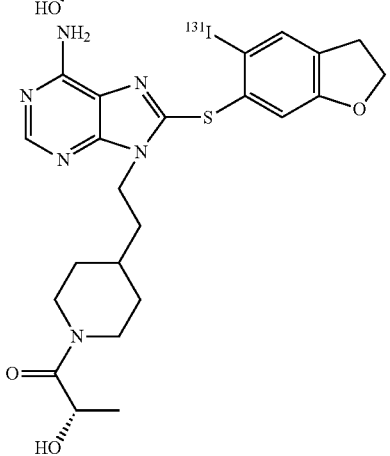

47
-continued
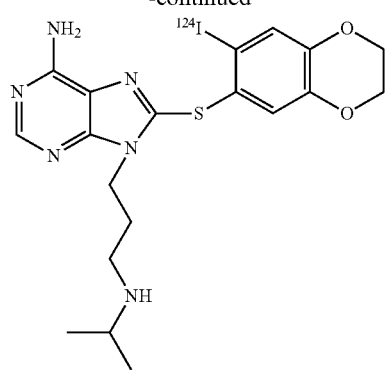
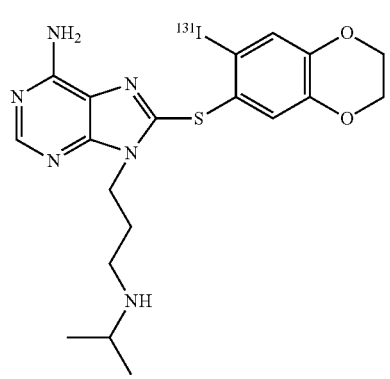
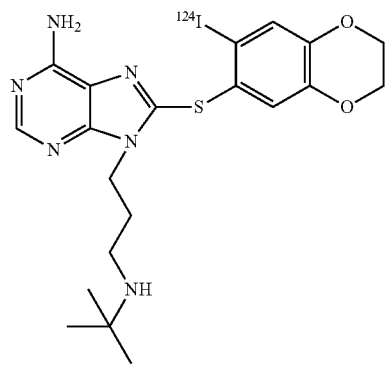
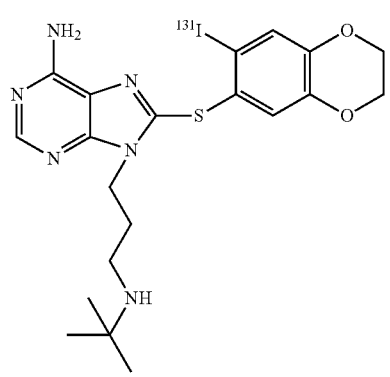
48
-continued
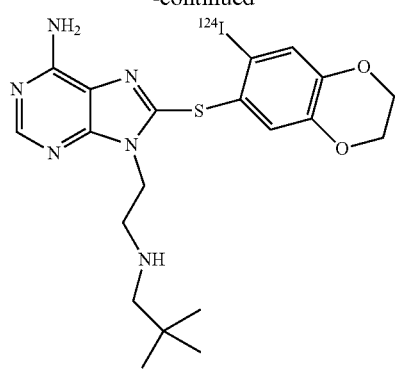
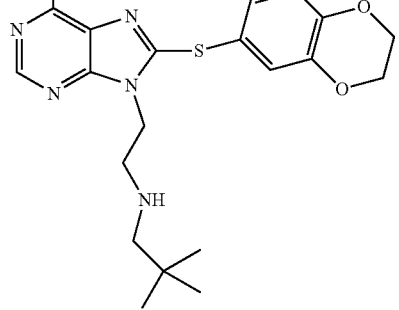
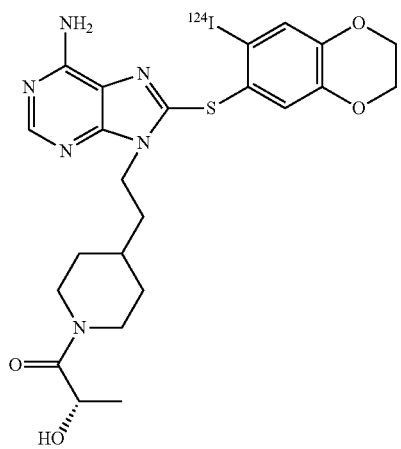
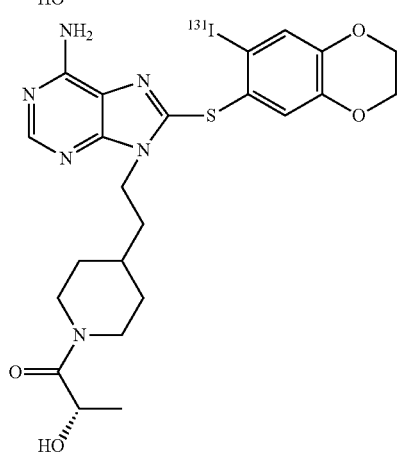
In some embodiments, a radiolabeled compound in a provided method is selected from a compound having the following formulae:

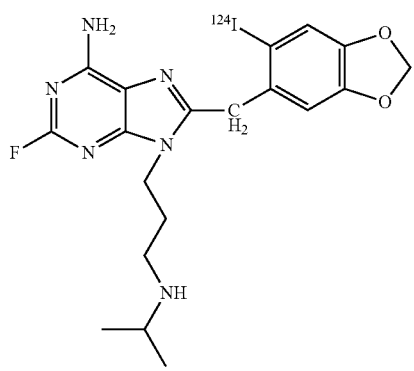
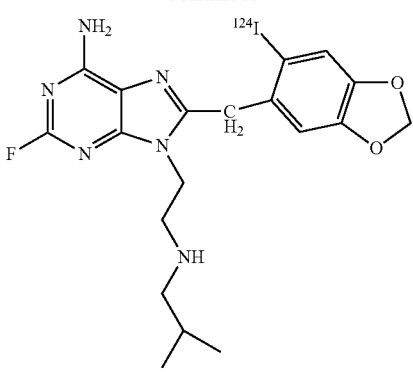
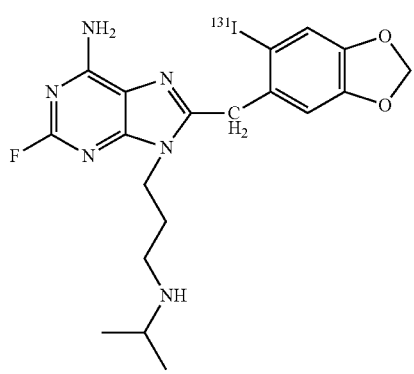
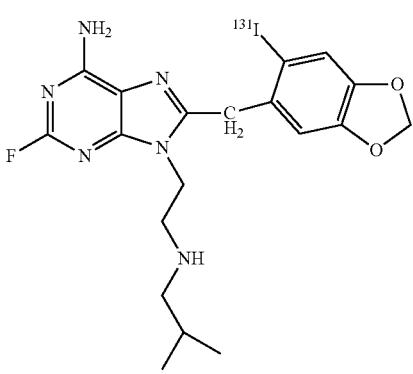
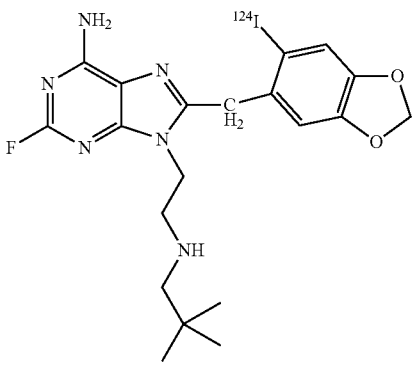
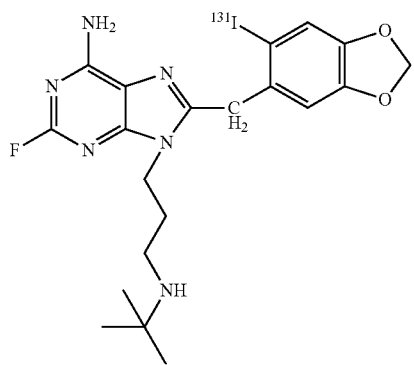
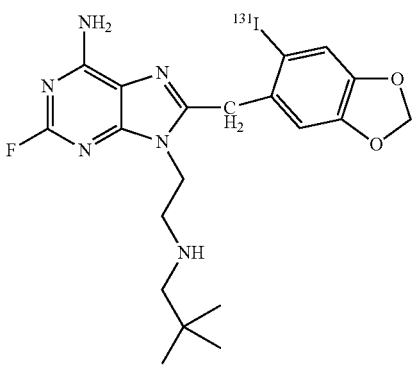

51
-continued
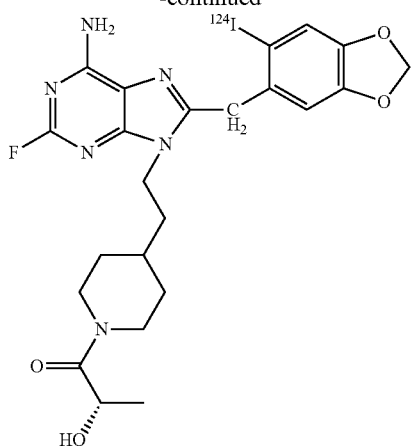
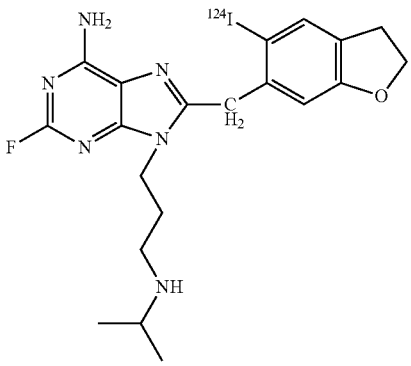
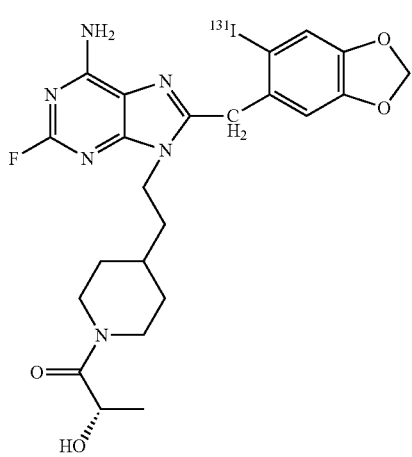
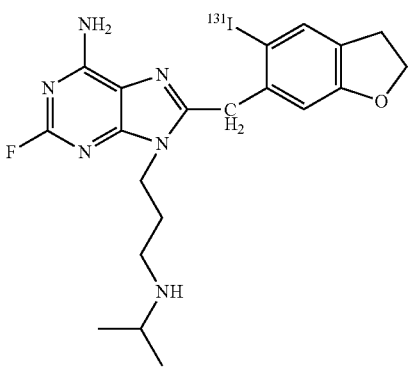
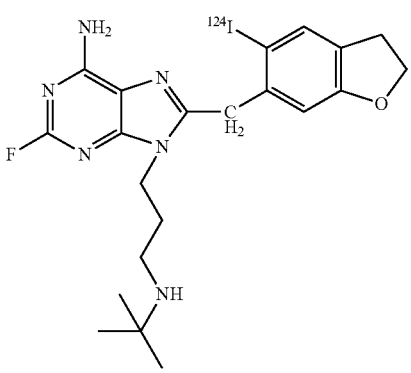
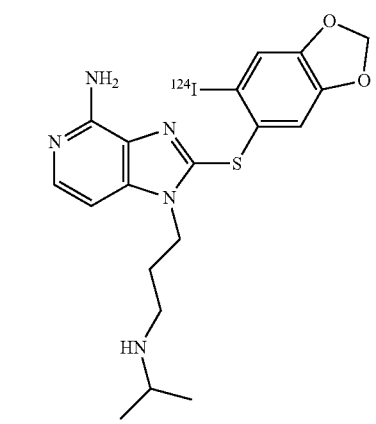
In some embodiments, a radiolabeled compound in a provided method is selected from a compound having the following formulae:
52
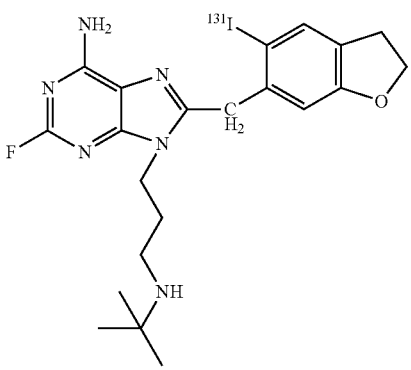

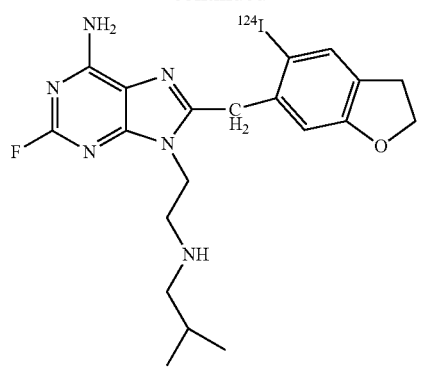
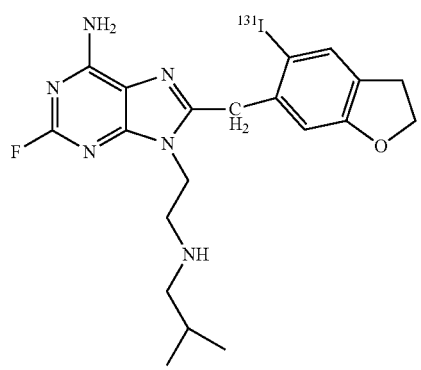
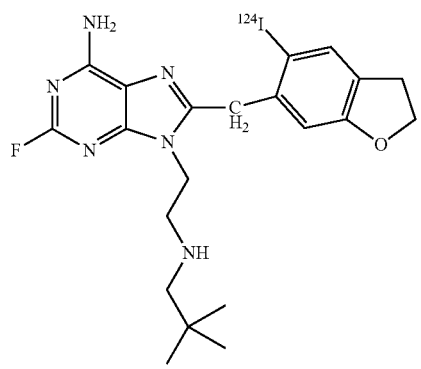
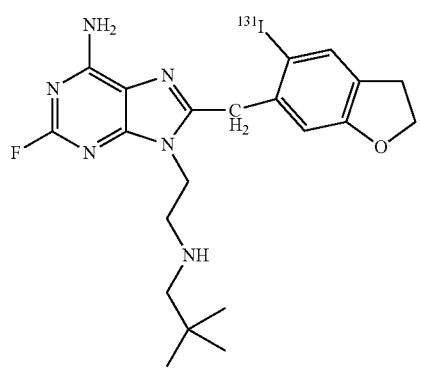
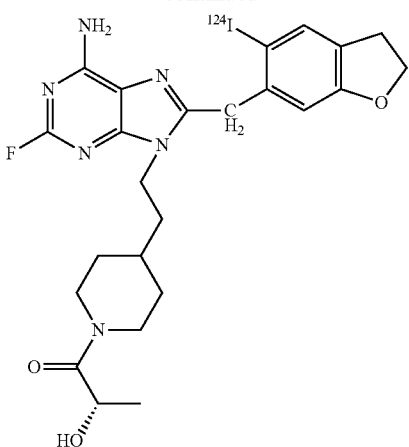
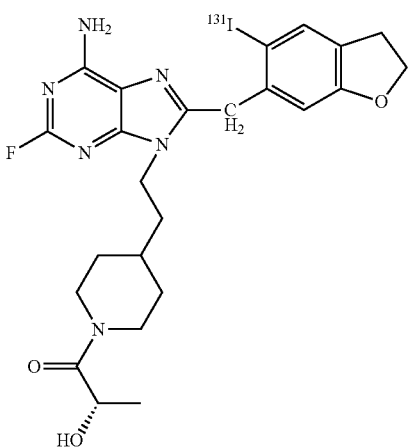
In some embodiments, a radiolabeled compound in a provided method is selected from a compound having the following formulae:
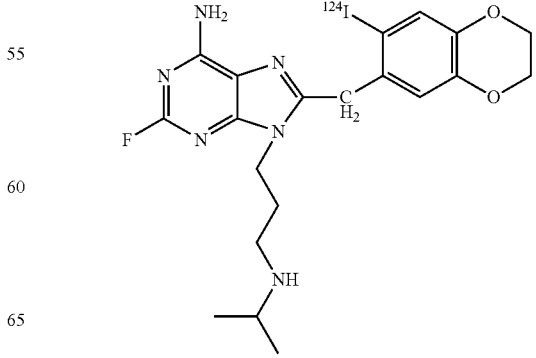

55
-continued
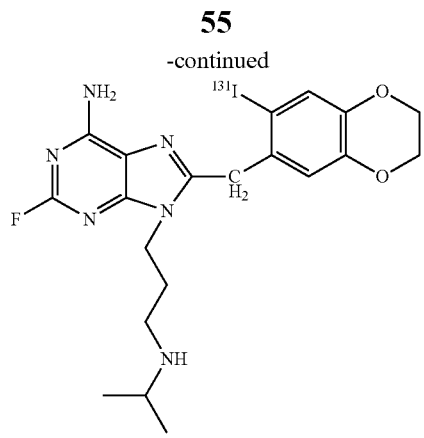
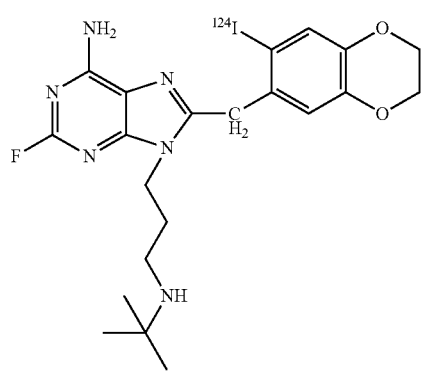
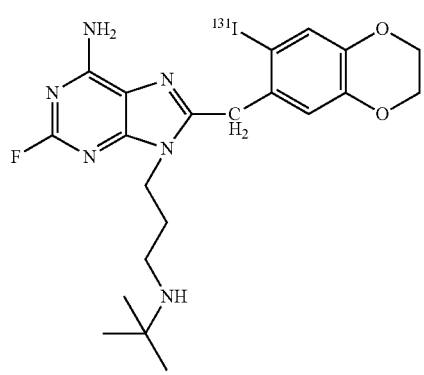
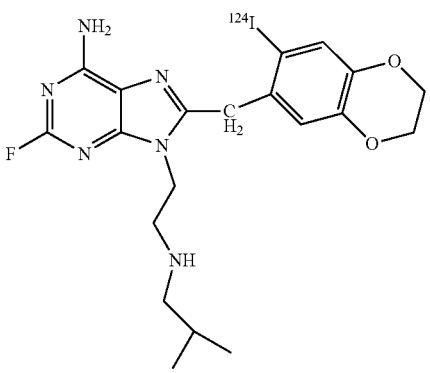
56
-continued
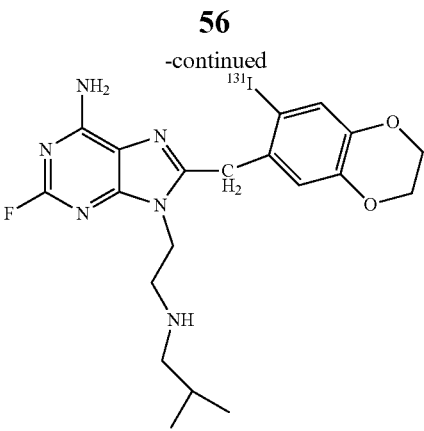
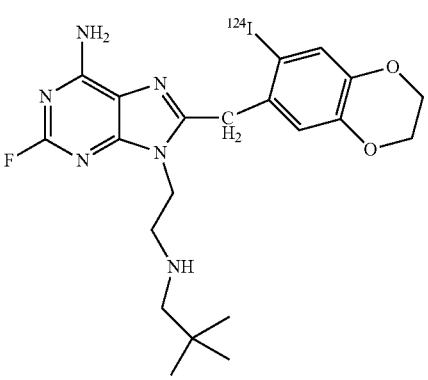
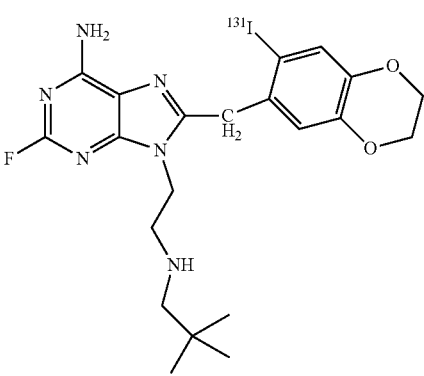
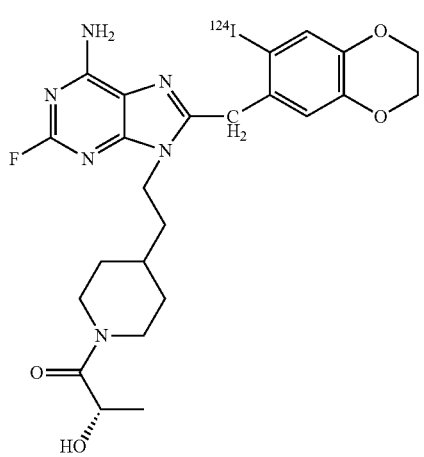

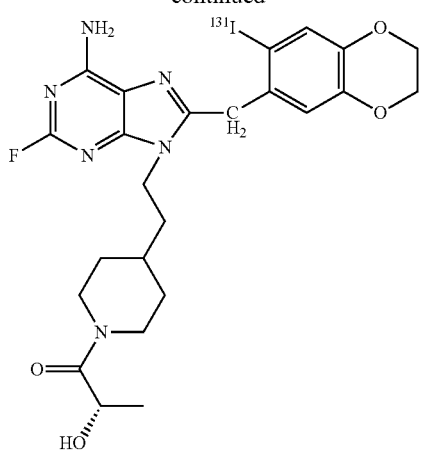
In some embodiments, a radiolabeled compound in a provided method is selected from a compound having the following formulae:
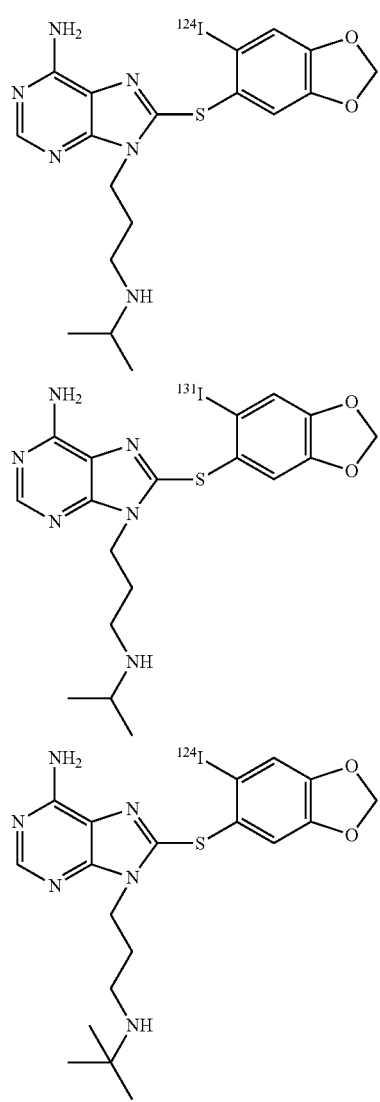
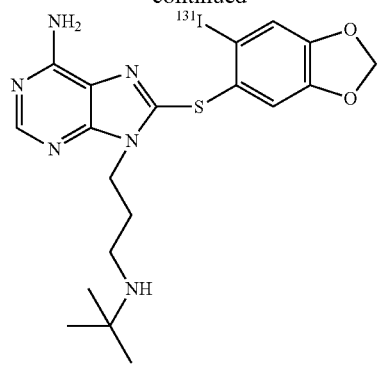
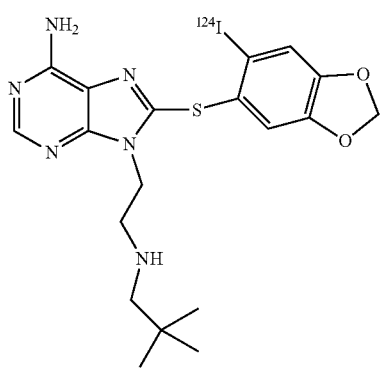
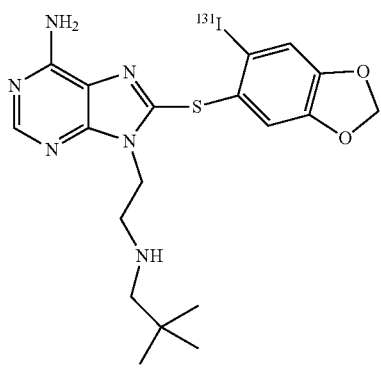
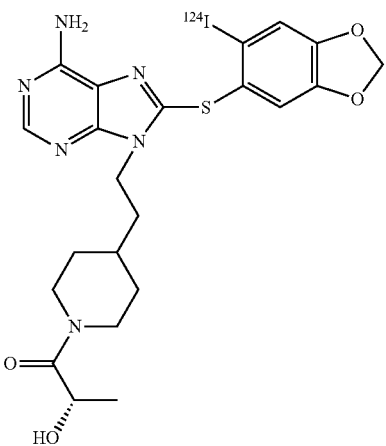

-continued
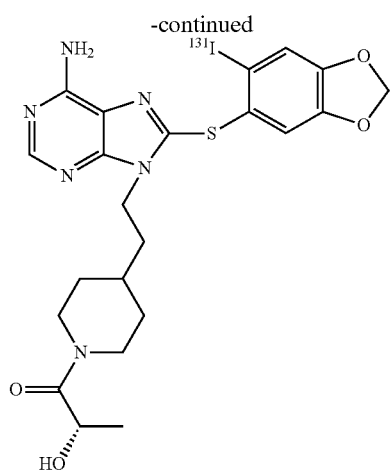
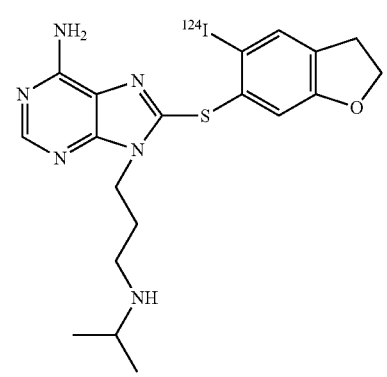
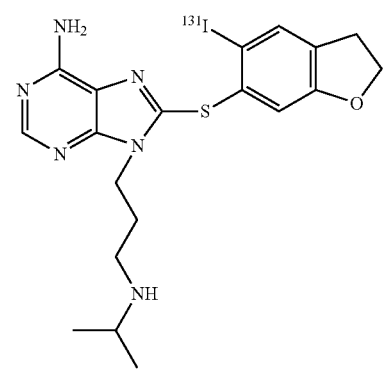
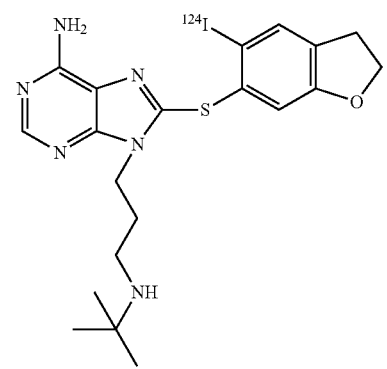
-continued
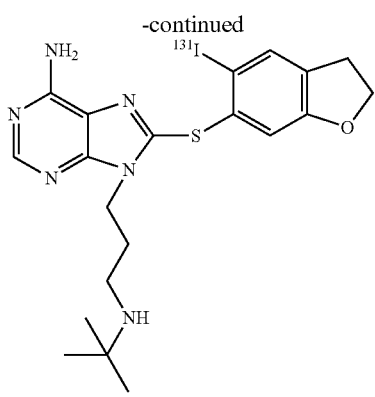
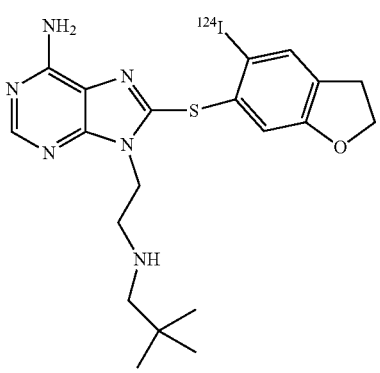
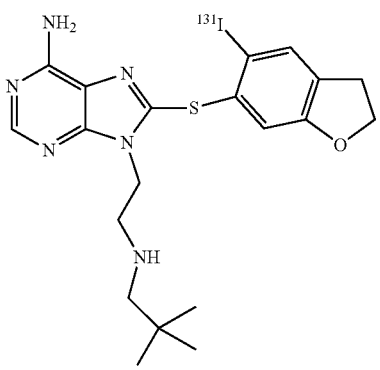
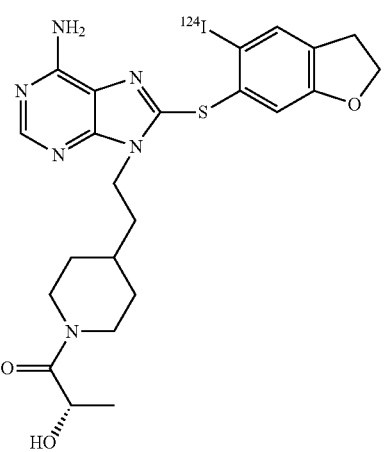

US 11,065,350 B2
61
-continued
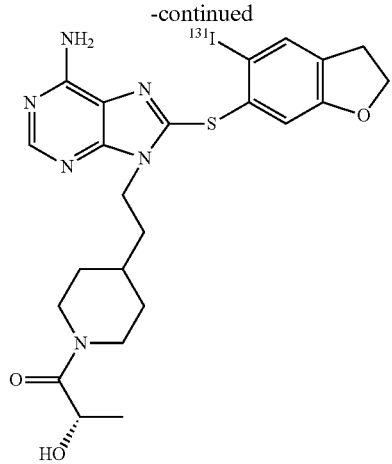
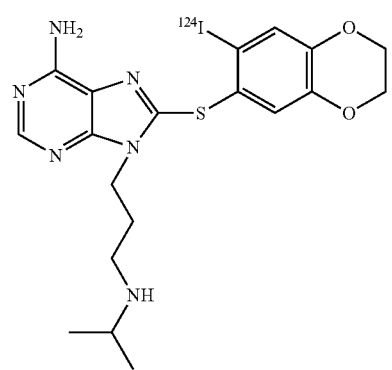
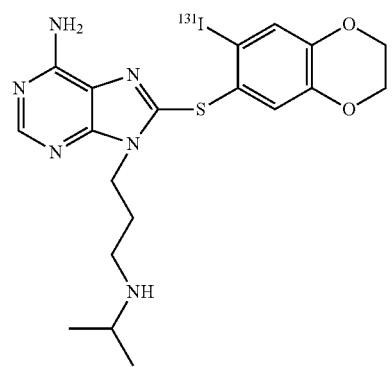
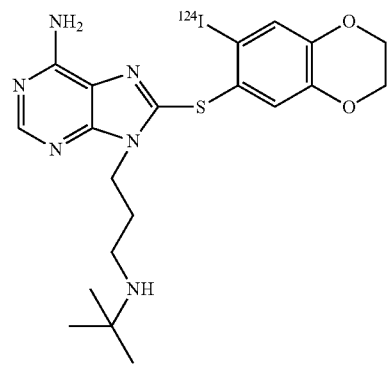
62
-continued
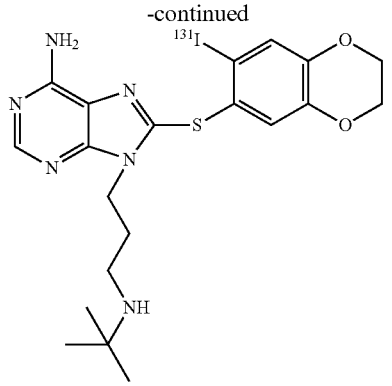
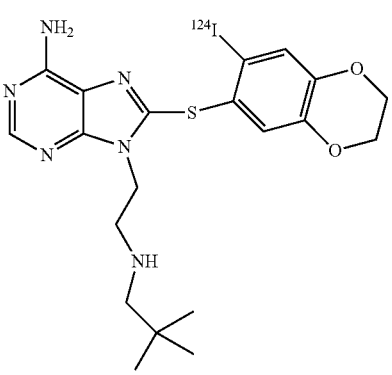
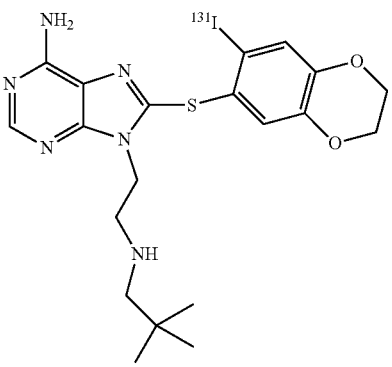
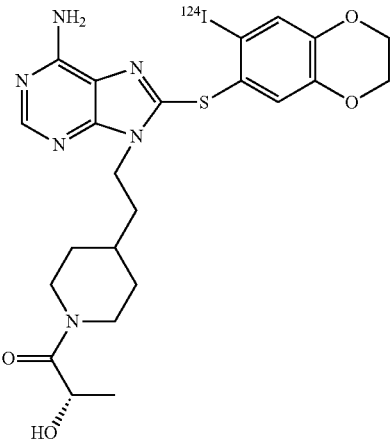

-continued

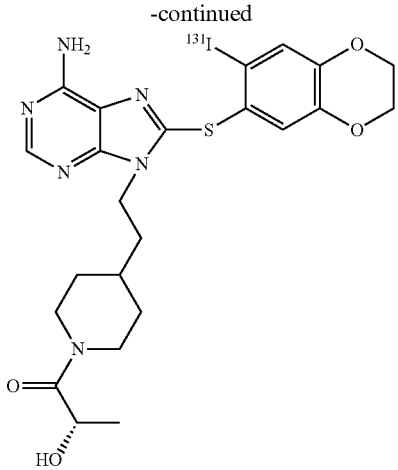

In some embodiments, a radiolabeled compound in a provided method is selected from a compound having the following formulae:

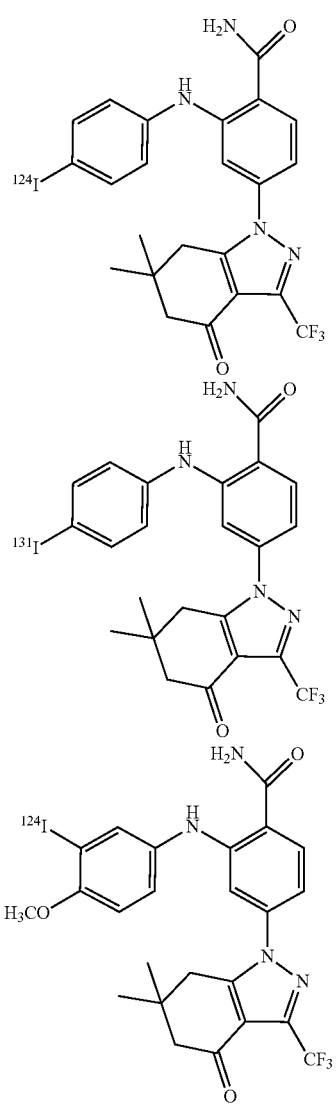

-continued

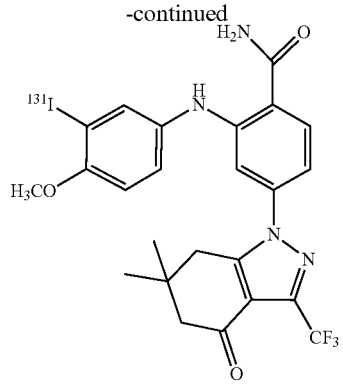

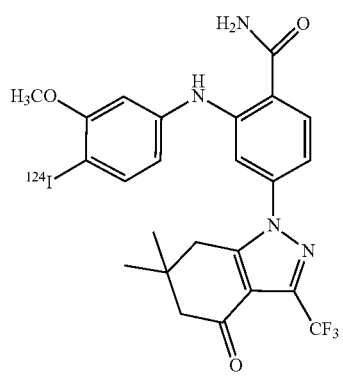

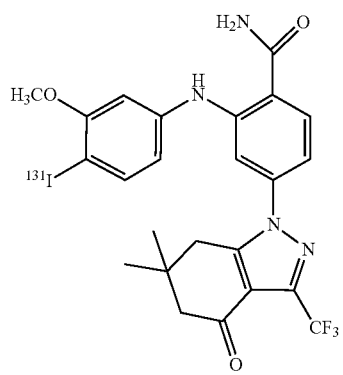

Methods of synthesizing the radiotracers in the above embodiments can be found for instance in U.S. Pat. No. 7,834,181, WO 2011/044394, WO 2008/005937 and PCT application PCT/US2012/032371, the contents of each of which are hereby incorporated by reference in their entirety.

EXEMPLIFICATION

Methods for preparing the labeled compounds are widely known in the art, for example but not limited to U.S. Pat. No. 7,834,181, the entirety of which is hereby incorporated by reference. Suitable imaging technologies, such as PET, SPECT and CT, and their combination with other imaging and/or diagnostic techniques, are widely known and practiced in the art as well.

Exemplary Procedure Using [124]I-PUH71
(Compound A with [124]I)

Positron emission tomography (PET) combined with X-ray computed tomography (CT) was performed using a state of the art integrated PET-CT scanner (Discovery DSTE™, General Electric). CT scans for attenuation correction and anatomic coregistration were performed prior to tracer-injection, using the following acquisition parameters: 140 kVp; 85 mA; pitch of 1.75:1; reconstructed slice thickness of 3.75 mm; 0.8 s per rotation. The CT protocol was designed for anatomic localization of tracer-signal and for attenuation correction, while minimizing radiation exposure. Each patient received~185 megabecquerel (MBq) [124]I-PU-H71 by peripheral vein over two minutes. PET emission scans were acquired in two-dimensional mode starting at the mid-thighs moving toward the head, for 7.5 minutes per PET bed position. PET data were reconstructed using a standard ordered subset expected maximization iterative algorithm. Emission data were corrected for scatter, attenuation and decay. Clinical FDG PET-CT studies were performed according to standard methods using state of the art PET-CT scanners. [124]I-PU-H71 scans were performed at 3-4 hrs, 20-24 hrs, 48-72 hours and, optionally, ~168 hrs after tracer administration on the microdose [124]I-PU-H71 PET-CT study. See FIGS. 1-2.

PU-PET images were taken 1.5, 4, 24 and 48-72 hrs after co-administration on the tracer mixed with a therapeutic dose of non-radioactive PUH71 in a total volume of 100 Ml, co-infused intravenously over one hour. Patient were treated with PU-H71 at escalating dose levels determined by a modified continuous reassessment model. Each patient is treated with his or her assigned dose on day 1, 4, 8 and 11 of each 21 day cycle. Pre- and post-treatment biopsies were collected for correlative studies including LCMSMS quantification of PU-H71, with the latter obtained within 24 hours of their cycle 1, day 1 dose of PU-H71. See FIGS. 3-4.

Synthesis of [124]I-PUH71

The general chemical scheme for the radiochemical synthesis of [124]I-PU-H71 is illustrated below. [124]I-NaI (~50 μL) was transferred to 1 mL reacti-vial and to it trimethyl tin precursor (Me3Sn-PU-H71) (25 μg) dissolved in 20 μL of methanol was added. To the resulting solution 15 μL of freshly prepared chloramine-T (1.5 mg/mL in acetic acid) was added and the reaction mixture was heated at 50° C. for 5 minutes. The vial was allowed to cool for 2 min and L of methionine methyl ester (0.5 g/mL) in water was added. Finally, 10 μL of concentrated HCl was added and the solution was heated at 50° C. for 30 min with occasional shaking. The reaction mixture was cooled to room temperature and purified using HPLC. The product was collected and the solvent was removed under reduced pressure using a rotary evaporator. The final product was formulated in 5% ethanol in saline (0.9%). 5% ethanol was used to avoid adherence of the minute amounts of tracer to the walls of the flask. Next, the solution was passed through 0.22 μm filter into pyrogen free vial equipped with a sterile vent. A portion of final formulation was withdrawn and used for quality control analysis.

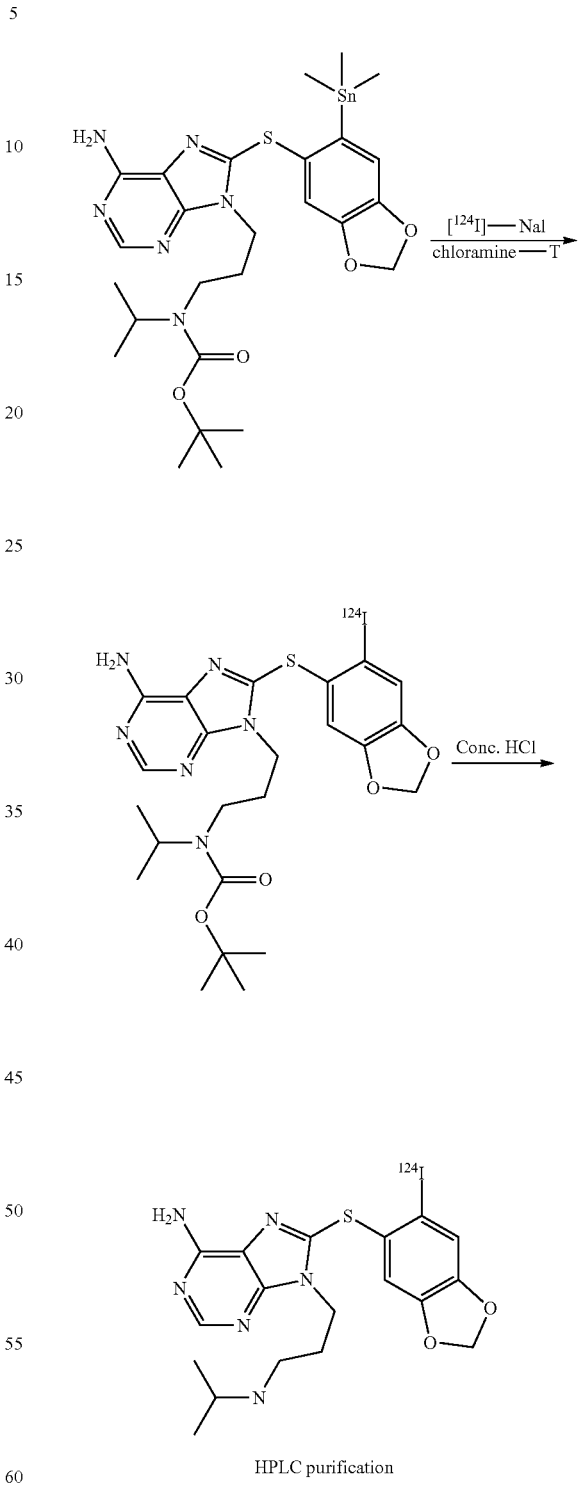

The invention claimed is:
1. A method for treatment of brain inflammation comprising administering to a subject in need thereof a compound having the formula:

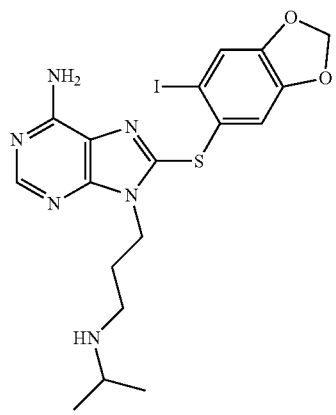

or a pharmaceutically acceptable salt thereof;

wherein the brain inflammation is not caused by cancer.

2. The method of claim 1, wherein the brain inflammation is a result of brain trauma.

3. The method of claim 1, wherein the method further comprises administration of anti-inflammatory agents, antihistamines, immunosuppressive agents, anti-viral agents, anti-fungal agents, antibacterial agents, anti-parasitic agents, or a combination thereof.

4. The method of claim 3, wherein administration of the anti-inflammatory agents, antihistamines, immunosuppressive agents, anti-viral agents, anti-fungal agents, antibacterial agents, anti-parasitic agents, or a combination thereof is subsequent to or prior to the administration of a compound having the formula:

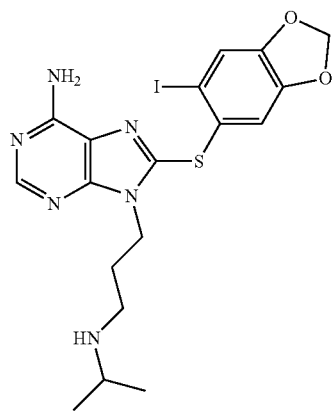

or a pharmaceutically acceptable salt thereof.

5. A method for treatment of inflammation comprising administering to a subject in need thereof a compound having the formula:

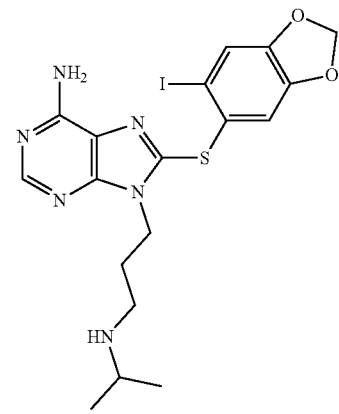 [SMILES: CC(C)NCCCn1c(Sc2cc3c(cc2I)OCO3)nc2c(N)ncnc21]

or a pharmaceutically acceptable salt thereof;

wherein the inflammation is not caused by cancer.

6. The method of claim 5, wherein the method further comprises administration of anti-inflammatory agents, antihistamines, immunosuppressive agents, anti-viral agents, anti-fungal agents, antibacterial agents, anti-parasitic agents, or a combination thereof.

7. The method of claim 6, wherein administration of the anti-inflammatory agents, antihistamines, immunosuppressive agents, anti-viral agents, anti-fungal agents, antibacterial agents, anti-parasitic agents, or a combination thereof is subsequent to or prior to the administration of a compound having the formula:

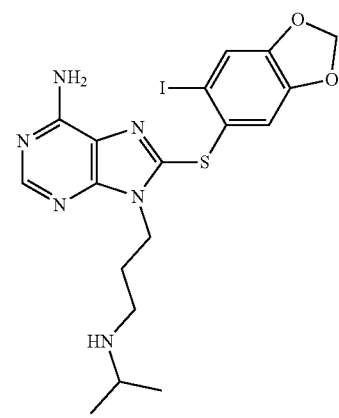 [SMILES: CC(C)NCCCn1c(Sc2cc3c(cc2I)OCO3)nc2c(N)ncnc21]

or a pharmaceutically acceptable salt thereof.

8. A method for treatment of lung inflammation comprising administering to a subject in need thereof a compound having the formula:

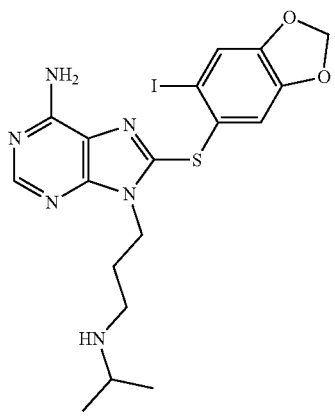 [SMILES: CC(C)NCCCn1c(Sc2cc3c(cc2I)OCO3)nc2c(N)ncnc21]

or a pharmaceutically acceptable salt thereof;
wherein the inflammation is not caused by cancer.

9. The method of claim 8, wherein the lung inflammation is a result of a lower or upper respiratory tract infection.

10. The method of claim 9, wherein the lower or upper respiratory tract infection is a viral infection.

11. The method of claim 8, wherein the subject is suffering from SARS or a common cold.

12. The method of claim 8, wherein the subject has a pulmonary infiltrate.

13. The method of claim 8, wherein the method further comprises administration of anti-inflammatory agents, antihistamines, immunosuppressive agents, anti-viral agents, anti-fungal agents, antibacterial agents, anti-parasitic agents, or a combination thereof.

14. The method of claim 13, wherein administration of the anti-inflammatory agents, antihistamines, immunosuppressive agents, anti-viral agents, anti-fungal agents, antibacterial agents, anti-parasitic agents, or a combination thereof is subsequent to or prior to the administration of a compound having the formula:

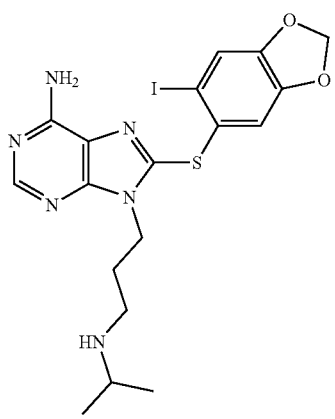 [SMILES: CC(C)NCCCn1c(Sc2cc3c(cc2I)OCO3)nc2c(N)ncnc21]

or a pharmaceutically acceptable salt thereof.

15. A method for treatment of a viral infection comprising administering to a subject in need thereof a compound having the formula:

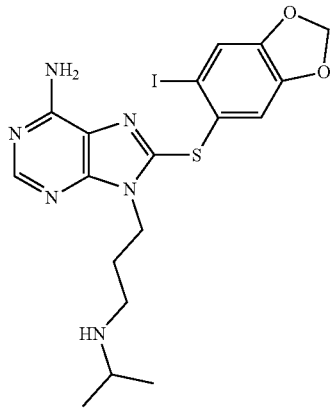 [SMILES: CC(C)NCCCn1c(Sc2cc3c(cc2I)OCO3)nc2c(N)ncnc21]

or a pharmaceutically acceptable salt thereof.

16. The method of claim 15, wherein the viral infection is a lower or upper respiratory tract infection.

17. The method of claim 15, wherein the subject is suffering from SARS or a common cold.

18. The method of claim 15, wherein the subject has a pulmonary infiltrate.

19. The method of claim 15, wherein the method further comprises administration of anti-inflammatory agents, antihistamines, immunosuppressive agents, anti-viral agents, anti-fungal agents, antibacterial agents, anti-parasitic agents, or a combination thereof.

20. The method of claim 19, wherein administration of the anti-inflammatory agents, antihistamines, immunosuppressive agents, anti-viral agents, anti-fungal agents, antibacterial agents, anti-parasitic agents, or a combination thereof is subsequent to or prior to the administration of a compound having the formula:

or a pharmaceutically acceptable salt thereof.

* * * * *